United States Patent [19]
Teichmann et al.

[11] Patent Number: 6,027,735
[45] Date of Patent: Feb. 22, 2000

[54] PRODUCTS AND PROCESSES FOR GASTRIC CASCADE AND GASTROINTESTINAL DISORDER TREATMENT WITH SAME

[75] Inventors: Reinhard K. Teichmann, Pfullingen; Hans-Georg Liebich, München; Walter Brendel, Planegg, all of Germany

[73] Assignee: EFFEM GmbH, Verden/Aller, Germany

[21] Appl. No.: 08/468,335

[22] Filed: Jun. 6, 1995

Related U.S. Application Data

[62] Division of application No. 08/307,943, Sep. 16, 1994, Pat. No. 5,725,861, which is a continuation-in-part of application No. 08/295,224, Aug. 24, 1994, abandoned, which is a continuation of application No. 08/132,490, Oct. 6, 1993, abandoned, which is a continuation of application No. 08/047,779, Apr. 15, 1993, abandoned, which is a continuation of application No. 07/921,461, Jul. 28, 1992, abandoned, which is a continuation of application No. 07/499,306, filed as application No. PCT/DE88/00724, Nov. 18, 1988, abandoned, said application No. 08/307,943, is a continuation-in-part of application No. 08/156,397, Nov. 22, 1993, abandoned, which is a continuation of application No. 07/846,221, Mar. 4, 1992, abandoned, which is a continuation of application No. 07/778,787, Oct. 18, 1991, abandoned, which is a continuation of application No. 07/180,475, Apr. 12, 1988, abandoned.

[51] Int. Cl.[7] .......................... A61K 39/07; A61K 39/00; A61K 7/00; A61K 47/30

[52] U.S. Cl. .................... 424/246.1; 424/184.1; 424/70.14; 424/70.22; 424/278.1; 514/2; 514/772.1; 530/833; 530/868; 530/825; 530/826

[58] Field of Search .................... 424/184.1, 70.14, 424/70.22, 246.1; 514/278.1, 2, 772.1; 530/833, 868, 825.26

[56] References Cited

U.S. PATENT DOCUMENTS

| | | |
|---|---|---|
| 4,822,611 | 4/1989 | Booren . |
| 4,879,113 | 11/1989 | Smith . |
| 5,023,077 | 6/1991 | Geras et al. . |
| 5,128,127 | 7/1992 | Beck . |
| 5,290,571 | 3/1994 | Bounous et al. . |
| 5,451,412 | 9/1995 | Bounous et al. . |
| 5,725,861 | 3/1998 | Teichmann et al. . |

FOREIGN PATENT DOCUMENTS

| | | |
|---|---|---|
| 3733899 | 6/1989 | Denmark . |
| 0059521 | 9/1982 | European Pat. Off. . |
| 0 219 979 | 4/1987 | European Pat. Off. . |
| 0 286 847 | 10/1988 | European Pat. Off. . |
| 0286847 | 10/1988 | European Pat. Off. . |
| 3733899 | 6/1989 | Germany . |
| 2 008 404 | 6/1979 | United Kingdom . |
| WO 86/07539 | 12/1986 | WIPO . |
| 8704050 | 7/1987 | WIPO . |
| WO 87/04050 | 7/1987 | WIPO . |
| WO 88/08699 | 11/1988 | WIPO . |

OTHER PUBLICATIONS

Fushiki et al, 1986, Chemical Abstracts, 104: 340 Reference # 85934W.
Teichmann et al, 1984, Chirurgisdies Forum, 84: 151–154.
Teichmann et al, 1983, Gastroenterology, 84(2): 1333.
Porter et al. Vet. Record. 1975, 97:24–28.
Andre et al. 1978, Allergy 33: 316–318.
Moon et al. 1995, Anals of Allergy, Asthama & Immuno. 74: 5–12.
Jost et al. 1987, Food Technology Oct.: 118–121.
Heppell et al. 1984, British J. Nutrition 51: 29–36.
Enomoto et al. 1993, Clin. Immunol. & Immunopath. 66(2):136–142.
Shay, H., et al., *Gastroenterology*, 5: 43–61, 1945.
Gregory, R.A., et al., *Gut*, 5: 103–117, 1964.
Grossmann, M.I., *Physiology of the Gatrointestinal Tract*, pp. 659–671, Ed.: L.R. Johnson, Raven Press, Ny.Y., 1981.
Sonnenberg, R., et al., *Gastroenterology*, 84: 1553, 1983.
Sauerbruch, T., et al. *Gastroenterology*, 90: 1998–2003, 1986.
Pratschke, E., et al., *Chirurgisches Forum '86*: 261–265, 1986.
Mimura et al. J. Phormacobio Dyn. 6/7: 449–458, 1983.
Rodriquez–Ollerus et al., Am. J. Gastroenterol, 56(1): 52–60, 1971.
Andre et al., Allergy, 33:316–318, 1978.
P. Porter et al., Vet Record 97(2), Jul. 12, 1975, pp. 24–28.
J. Klimowski et al., Arch Immunol Ther Exp. 28(1), 1980, pp. 88–92.
H.J.F. Hodgson, Agents and Action 1992, pp. 27–31.
Arthur C. Guyton, M.D., (1981 *Textbook of Medical Physiology*, W.B. Saunders Co., Philadelphia, pp. 784–815 and 827–835).

*Primary Examiner*—Nita Minnifield
*Attorney, Agent, or Firm*—Fitzpatrick, Cella, Harper & Scinto

[57] ABSTRACT

The present invention provides a method and products for establishing nutrient recognition and improving nutrient utilization and growth in a human or an animal by immunologically stimulating digestion or a gastric cascade within the gastrointestinal tract, by orally or parenterally immunizing the human or animal with an immunizing effective amount of an ingestible antigen or a mixture of ingestible antigens and orally reintroducing the antigen(s). Another aspect of the invention provides a method and products for preventing and treating gastrointestinal disease by immunologically stimulating a gastric cascade, namely, blood flow, production of mucus and release of digestion regulatory factors within the gastrointestinal tract of a human or an animal, by orally or parenterally immunizing the human or the animal with an immunizing effective amount of an ingestible antigen or a mixture of ingestible antigens and orally reintroducing the antigen(s). More generally, the invention provides a process, as well as products, for stimulating a gastric cascade in an animal or human. The gastric cascade is useful for preventing or treating gastrointestinal disorders, including ulcers, as well as for improving nutrient utilization, growth and/or resistance; the latter being inclusive within the term "gastrointestinal treatment".

26 Claims, 22 Drawing Sheets

REGULATION OF ANTIGEN STIMULATED
GASTRIN RELEASE

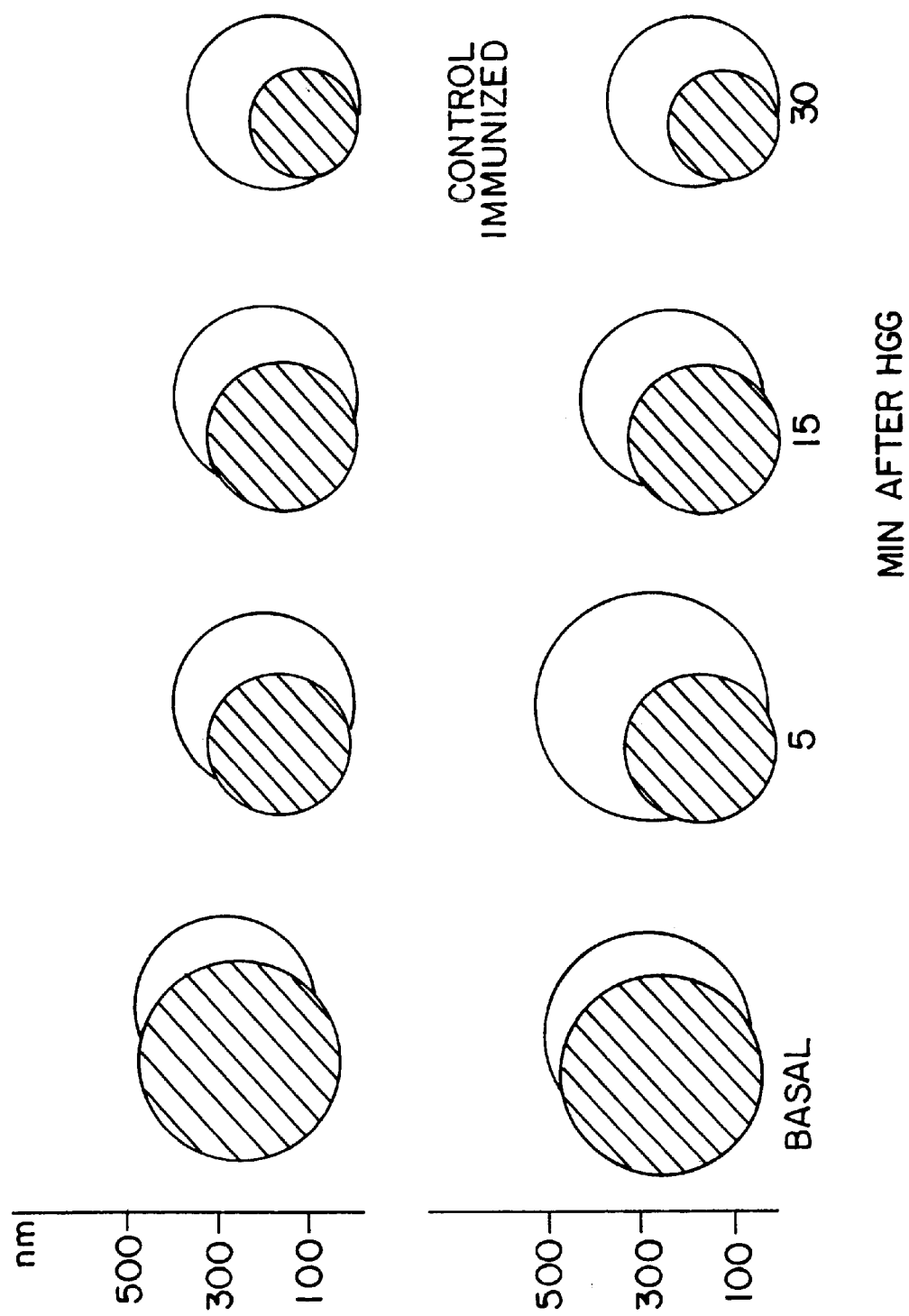

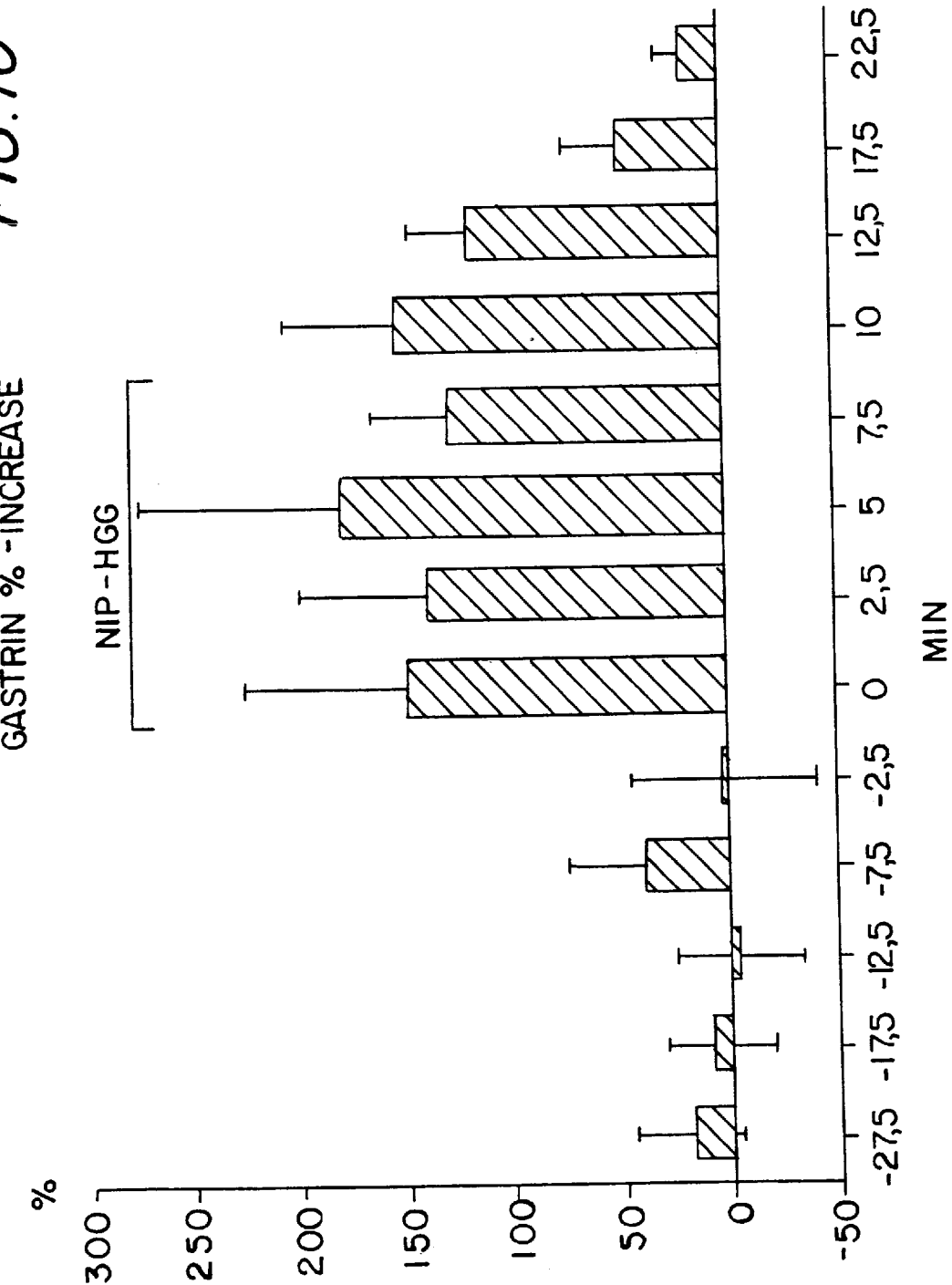

FIG. 13

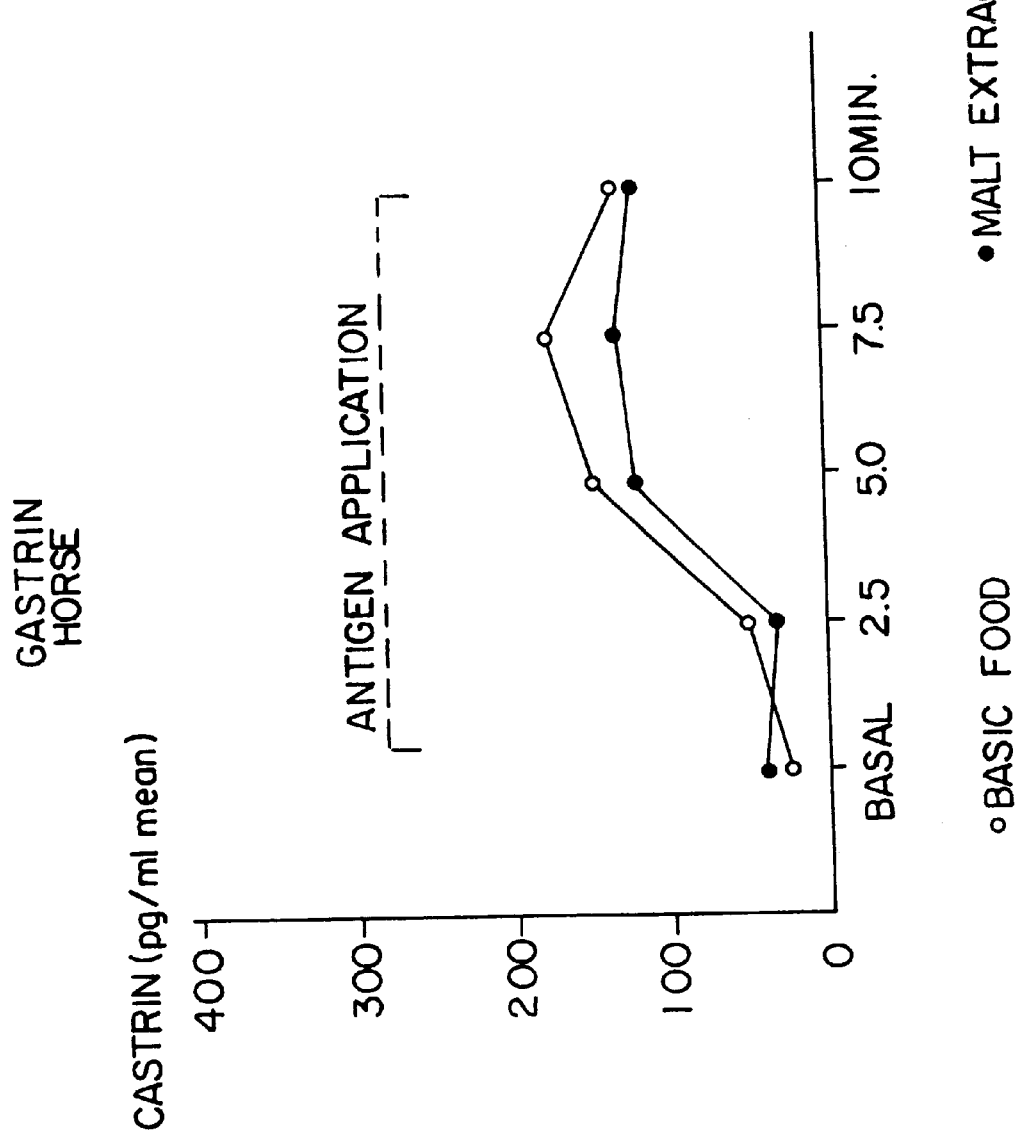

PRODUCTS AND PROCESSES FOR GASTRIC CASCADE AND GASTROINTESTINAL DISORDER TREATMENT WITH SAME

RELATED APPLICATIONS

This application is division of allowed application Ser. No. 08/307,943, filed Sep. 16, 1994 U.S. Pat. No. 5,725,861, which is a continuation-in-part of application Ser. No. 08/295,224, filed Aug. 24, 1994, now abandoned, which is a continuation of application Ser. No. 08/132,490, filed Oct. 6, 1993, now abandoned, which is a continuation of application Ser. No. 08/047,779 filed Apr. 15, 1993, now abandoned, which is a continuation of application Ser. No. 07/921,461 filed Jul. 28, 1992, now abandoned, which is a continuation of application Ser. No. 07/499,306 filed May 16, 1990, now abandoned, which in turn is the National Phase of PCT/DE88/00724, filed Nov. 18, 1988 and designating the U.S. Allowed application Ser. No. 08/307,943 is also a continuation-in-part of application Ser. No. 08/156,397 filed Nov. 22, 1993, now abandoned, which is a continuation of application Ser. No. 07/846,221 filed on Mar. 4, 1992, now abandoned, which in turn is a continuation of application Ser. No. 778,787, filed Oct. 18, 1991, now abandoned, which is a continuation of application Ser. No. 180,475, filed Apr. 12, 1988, now abandoned, which claims the benefit of priority under 35 U.S.C. §119 of German application P3712890.6, filed Apr. 15, 1987. Each of the above-recited applications is hereby expressly incorporated herein by reference. No admission is made as to any issues in the prosecution of the above-cited applications.

FIELD OF THE INVENTION

The present invention relates to new methods of establishing nutrient recognition and thereby increasing nutrient utilization and growth in animals, including humans, .through the induction of an immune response within the gastrointestinal tract to stimulate normal digestive processes. Normal digestive processes stimulated by an immune response include a release of digestive enzymes and acids, secretion of mucus into the stomach, an increase in blood flow to the gastrointestinal tract and a release of digestion regulatory factors into the bloodstream. The present invention also relates to a method for preventing and treating gastrointestinal diseases such as colic, diarrhea, constipation, intestinal gas, gastric erosions, gastric ulcers and intestinal ulcers by immunologically stimulating digestive processes such as blood flow, production of mucus and release of digestion regulatory factors within the gastrointestinal tract of an animal.

BACKGROUND OF THE INVENTION

Current methods for improving growth, nutrient utilization and disease resistance in animals rely on antibiotics, hormones and antimicrobials. The feed additives used for many decades and other processes for promoting animal growth and for improving nutrient utilization have had limited success and, the use of these substances is increasingly challenged worldwide. For example, antibiotics in feeds may not only lead to irreparable damage to animal health through the increasing formation of resistant pathogen strains with the danger of secondary diseases, but also may be dangerous to the health of humans, as the final consumers of foods of animal origin. The use of antibiotics in animals is blamed for the emergence of resistant strains of pathogens which pose a direct threat to man. Hormones may cause even greater damage to animal and human health, among other reasons, because of their anabolic promotion of the growth rate. The hormones may not be excreted from the animal body to the desired extent resulting in residues in edible tissues. Furthermore, antimicrobials can be carcinogenic or have co-carcinogenic effects on animals. As a result, many products used by farmers in the past to promote animal health, growth and nutrient utilization have been banned or subjected to curtailed application by government decree.

Since the usual products and processes show these numerous, health-damaging disadvantages and since no other suitable processes relating to commercially used feed are known, there is an increasing need for new methods and products to regulate digestion and improve growth, nutrient utilization and disease resistance in animals. Ideally these methods should be natural methods employing natural products that create no residues or adverse side effects. Moreover, a method should be effective in many types of species and in any age group. These methods should also be applicable to man for use in preventing malnutrition due to limited food supply, or to assist in recovery of debilitated patients.

Application of methods for improving nutrient utilization and regulating digestion have widespread implications. For example, when digestion is not properly stimulated, release of gastric enzymes and acids is diminished and the pH within the stomach is not sufficiently acidic to kill pathogenic microbes. Such microbes can cause a multitude of symptoms including colic, diarrhea, constipation and related diseases. These types of diseases have been observed in farm animals, especially pigs, because the acidity of fluids within the stomach typically reaches only about pH 5.6 to 5.7, whereas a pH of about 5.2–5.4 is needed to kill most pathogens (Kirchgessner et al. 1991 Zbl.f.Hygiene 191: 265–276). Currently, organic acids such as formic acid and citric acid are added to animal feed, especially pig feed, to lower the acidity of stomach fluids to the degree needed to kill pathogens. However, the presence of such organic acids in animal feed can have undesirable side effects. For example, use of such organic acids may cause or exacerbate gastric or intestinal ulcers. Therefore, new methods of stimulating normal digestive processes are urgently needed in the animal production industry.

Moreover, many other types of gastrointestinal disorders including ulcers and gastric erosions can occur as a result of improper regulation of digestive processes and could be prevented or treated if normal regulation of digestive processes could be reestablished. Such diseases represent a significant health problem worldwide. For example, approximately 8–10% of North Americans have recurring problems with peptic ulcers and total costs for treatment represent about 1% of national health care expenses in the United States. Moreover, the mortality rate of patients suffering from peptic ulcers has not decreased significantly since 1952, whereas mortality in women having gastric and duodenal ulcers has actually increased (Sonnenberg et al. 1983, Gastroenterology 84: 1553).

Some current methods of regulating digestion to treat ulcers rely on drugs like muscarinic and histamine $H_2$ antagonists which are used to inhibit gastric acid secretion (Bauerfeind et al. 1986 Ulcustherapie JAMA 2: 135; Grossman, M. I. 1981, Regulation of gastric acid secretion. In: Physiology of the Gastrointestinal Tract, Ed. L. R. Johnson Raven Press, New York). However, these antagonists have undesirable side effects and frequently do not cure gastrointestinal disorders such as ulcers since many patients diagnosed as having ulcers and treated with these antagonists experience reoccurring symptoms within three years (DMW lll.Jg.Nr. 3, 1986).

Ulcers are a serious problem not only in human medicine but also in veterinary medicine, especially in pig, poultry, horse and cattle production, and in dogs and cats. For example, it is common for piglets to develop ulcers which can be lethal after weaning and a change to semi-liquid high energy diet. Within the European Common Market there are about 120,000,000 to 160,000,000 pigs raised annually and about the same number in North America.

Three to four percent are affected by severe ulcers which lead to death of the animal. Based upon these figures, about 4 million pigs per year are lost in Europe and in North America because of gastrointestinal disorders, resulting in a financial loss of up to 4 billion dollars per year. Similar losses occur in cattle and poultry farming as a result of gastrointestinal disease. Accordingly, there is an urgent need for new, safe and effective procedures to prevent and treat gastrointestinal diseases in both humans and animals.

Furthermore, there is a need for products and processes for increasing the growth rate and/or utilization of feeds and foods and/or resistance in animals and humans.

SUMMARY OF THE INVENTION

The present invention is directed to a discovery that immune responses within the gastrointestinal tract initiate and regulate digestion. Moreover, the present invention provides simple, safe and effective methods of stimulating and regulating digestion by immunization and subsequent feeding of an animal with an ingestible antigen. After immunization, the ingestible antigen can be fed or can be eaten to induce an immune response within the stomach which initiates digestion, increases blood flow to the stomach and stimulates the secretion of digestive acids and enzymes within the gastrointestinal tract. This effect caused by readministering the antigen may be called a "gastric cascade." The present invention is also directed to the surprising discovery that immunization of animals with an ingestible antigen followed by routine inclusion of that antigen in the diet, results in larger and healthier animals having less gastrointestinal disease. Accordingly, the methods of the present invention can be used to improve nutrient utilization and growth of animals as well as to prevent and treat gastrointestinal diseases; and, to increase growth rate and/or resistance.

More particularly, digestion is immunologically regulated by immunization with an ingestible antigen followed by routine feeding of the antigen. Upon immunological recognition of an antigen within the stomach, immune cells induce an increase in blood flow and production of mucus and as well as a release of digestion regulatory factors, digestive enzymes and acids within the gastrointestinal tract. Utilization of these methods has greatly reduced the incidence of gastrointestinal disease in a variety of animals. Accordingly, nutrient utilization, growth rate and resistance are also improved or increased.

Significantly, the present methods of improving nutrient uptake and growth in animals and of preventing and treating gastrointestinal disease are simple, inexpensive and do not rely on drugs or hormones that have adverse side effects.

The present invention provides a method for improving nutrient utilization and growth in a human or an animal by immunologically stimulating digestion within the gastrointestinal tract of the human or the animal, by orally or parenterally immunizing a human or an animal with an immunizing effective amount of an ingestible antigen or a mixture of ingestible antigens and orally reintroducing an effective amount of the antigen(s).

Another aspect of the invention provides a method for preventing and treating gastrointestinal disease by immunologically stimulating a gastric cascade, that is, blood flow, production of mucus and release of digestion regulatory factors within the gastrointestinal tract of a human or an animal, by orally or parenterally immunizing a human or an animal with an immunizing effective amount of an ingestible antigen or a mixture of ingestible antigens and orally reintroducing an effective amount of the antigen(s).

A further aspect of the present invention provides a method for improving nutrient utilization and growth in an animal such as a farm animal by immunologically stimulating digestion within the gastrointestinal tract of the animal, by orally and/or parenterally immunizing the animal with immunizing effective amount of a feed antigen or a mixture of feed antigens and subsequently feeding an effective amount of the feed antigen(s) to the animal.

A still further aspect of the invention provides a compartmentalized kit for immunization of a human or an animal according to the methods of the present invention.

BRIEF DESCRIPTION OF THE DRAWINGS

A better understanding of the present invention will be had by referring to the accompanying drawings, in which:

FIG. 8 shows the diameter of secretory granules in non-immunized animals (open circles) and animals immunized with human gamma globulin (dark circles) (The relative sizes of both superficial (top row) and basal (bottom row) mucus cells at several time points after antigenic stimulation with human gamma globulin (HGG) are depicted);

FIG. 10 shows the percent increase in gastrin released from the gastric mucosa of rats previously immunized with a synthetic antigen, 4-hydroxy-3-iodo-nitrophenyl acetic acid (NIP), upon exposure of the mucosa in vitro to NIP bound to a carrier protein (NIP-HGG) (over time);

FIG. 13 shows the percent increase in somatostatin released from the gastric mucosa of humans previously immunized with a microbial antigen, tetanus toxoid, upon in vitro exposure of the mucosa to this microbial antigen (over time) (Mucosa specimens from six patients were tested (i.e. n=6));

DETAILED DESCRIPTION OF THE INVENTION

Figure 1:
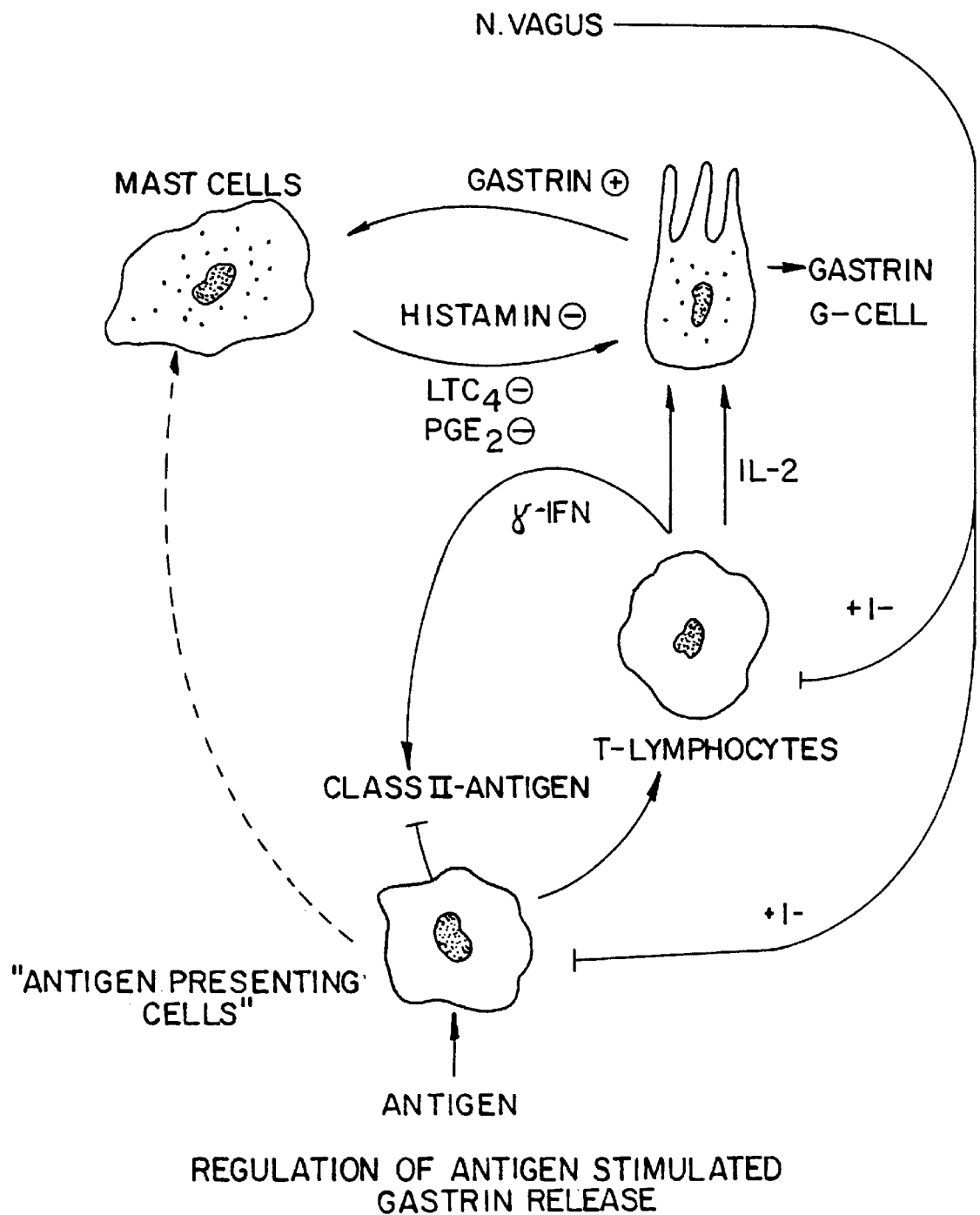
FIG. 1 schematically shows the regulation of antigen stimulated gastrin release.

The present invention relates to the surprising discovery that normal digestive processes are initiated by an immunological response to ingested antigens. Such an immunological response not only leads to a release of digestive enzymes and acids but also stimulates a gastric cascade, namely blood flow to the gastrointestinal tract, a massive discharge of mucus from cells in the stomach wall and a release of hormones which control and ultimately terminate release of acids and digestive enzymes. Therefore, induction of an immune response serves not only to initiate digestion but also to stimulate functions within the gastrointestinal tract that protect gastric and intestinal mucosal tissues and that terminate digestive processes.

The present invention provides a method for improving nutrient utilization and growth in a human or an animal by immunologically stimulating digestion within the gastrointestinal tract of the human or the animal by:

orally and/or parenterally immunizing the human or the animal with an immunizing effective amount of an ingestible antigen, or a mixture of ingestible antigens; and orally reintroducing an effective amount of said antigen(s) to immunologically induce an immune reaction within the gastrointestinal tract to stimulate digestion and improve nutrient utilization and growth in the human or the animal.

Moreover, the present invention provides a method for preventing and treating gastrointestinal disease by immunologically stimulating blood flow, production of mucus and release of digestion regulatory factors within the gastrointestinal tract of a human or an animal, by:

orally and/or parenterally immunizing the human or the animal with an immunizing effective amount of an ingestible antigen, or a mixture of ingestible antigens; and orally reintroducing an effective amount of said antigen(s) to immunologically induce an immune reaction within the gastrointestinal tract and thereby stimulate blood flow, production of mucus and release of digestion regulatory factors within the gastrointestinal tract of the human or the animal.

In the present invention, an animal is any vertebrate organism having an immune system which is capable of producing detectable levels of antibodies after immunization with an antigen. Animals contemplated by the present invention include humans, farm animals, birds, laboratory animals, zoo animals, aquatic animals, and any warm-blooded animal, domesticated animal or bird.

As used herein, farm animals include pigs, cattle, dairy cows, horses, goats, sheep, chickens, turkeys, geese, ducks and related species. Laboratory animals include rats, mice, guinea pigs, rabbits, goats, monkeys, dogs, cats and others. Zoo animals include all vertebrate animals kept in zoos. Aquatic animals include fish, eels, turtles, seals, penguins, sharks, whales, and related species. Domesticated animals include any pet, especially cats and dogs, or animal that is kept by humans, e.g., horses, cattle, pigs, goats, rabbits, chickens, turkeys, geese, ducks and the like.

The methods of the present invention are preferably practiced on humans and animals such as cattle, horses, pigs, goats, sheep, dogs, cats, rats, mice, monkeys, minks, rabbits, chickens, turkeys, geese, ducks, fish and related species. Preferred fish include trout, salmon, carp, catfish, talapia and other fish raised domestically.

Preferred farm animals are pigs, cattle, horses, goats, sheep, chickens, turkeys, ducks, geese, trout, salmon, carp, talapia and related animals. Especially preferred farm animals are pigs, cattle, chickens, turkeys, ducks and geese.

According to the present invention the term pigs includes pigs, piglets, hogs, gilts, barrows, boars and sows. Moreover, the term cattle includes calves, cows, dairy cows, heifers, steers and bulls.

In one preferred embodiment of this invention the present methods are practiced on baby humans or baby animals. Baby humans are infants and young children that are about 0 to 24 months old. Baby animals are 0 to 24 months old or are unweaned or recently weaned animals. Unweaned animals are animals receiving mother's milk by nursing or receiving a liquid formula that substitutes for mother's milk. Recently weaned animals have been weaned or have not received mother's milk or formula for 0 to 12 months. Preferred baby animals are piglets, calves, lambs, foals, kids (i.e. baby goats), chicks, baby turkeys, ducklings, goslings and hatchling fish. Preferred hatchling fish are trout, salmon, catfish, talapia, carp and other commercially produced fish. Especially preferred baby animals are piglets, calves, lambs, and foals.

As used herein, gastrointestinal tract refers to the alimentary canal of a human or an animal, including the mouth, esophagus, stomach and intestines as well as all associated blood vessels, lymph, endocrine and exocrine tissues.

Moreover, as used herein immune cells are antibody-producing cells, e.g., lymphocytes. Antibody-producing cells can produce antibodies as secreted antibodies or as membrane bound antibodies.

According to the present invention, digestion regulatory factors are any substances released by tissues of the animal that influence blood flow, mucus secretion and release of acid and digestive enzymes within the gastrointestinal tract. Such factors are generally exocrine or endocrine factors released by tissues associated with the gastrointestinal tract and can include gastrin, somatostatin, secretin, histamine, leukotriene C4, gamma-interferon, interleukin-1, interleukin-2 and related substances (Pratschke et al. 1985 Langenbecks Arch. Chir. Suppl. 295; Pratschke et al. 1985 Regulator der Gastrinfreisetzung. In: Kongreßbericht der 26. Jahrestagung der osterr. Gesellschaft für Chirugie. Eds: Helmer et al. Springer-Verlag, Groz 131). Digestion regulatory factors having an especially important role in gastrointestinal disease include gastrin, somatostatin, histamine and secretin.

According to the present invention, an ingestible antigen is any non-toxic substance which can be eaten by a human or fed to an animal and which has the capacity to stimulate a detectable immune response within the bloodstream and/or at the gastric mucus membrane. Preferred ingestible antigens are proteins, carbohydrates or glycoproteins, as well as small synthetic haptens. In some cases, a preferred ingestible antigen may be an antigen to which the human or the animal has never been exposed. Ingestible antigens as used herein can be plant, animal, microbial, or synthetic substances.

Plant antigens are derived from plants and preferably include vegetable or grain products, for example, any vegetable, soy, wheat, oats, corn, rye, barley, sorghum, alfalfa, clover, hops, hay and others. Preferred plant antigens, especially for farm animals, are grain products. Especially preferred plant antigens for domestic farm animals are soy, corn or sorghum.

Animal antigens include any antigenic substance derived from an animal. Animal antigens can be from cold blooded animals e.g., fish, shellfish and related aquatic animals, as well as from warm-blooded animals. In particular, the present invention contemplates using any meat, blood, egg or milk product derived from a warm blooded or cold-blooded animal as an ingestible antigen. Preferred animal antigens are from the milk or blood of any animal, from fish or from the eggs of any warm-blooded or cold-blooded animal. An especially preferred animal antigen for domestic farm animals is whey.

Microbial antigens are derived from any microbial organism including viruses and one-celled organisms. Examples of microbial organisms from which a microbial antigen can be derived include viruses, bacteria, fungi and related organisms. Preferably, microbial antigens are microbially-secreted products or substances on the surface of the microbe which are capable of eliciting a detectable immune response upon immunization of the animal with the intact microbe. Sources for microbial antigens include antigens from commonly ingested microbes like yeast, *Escherichia coli, Bacillis subtilis* and nonpathogenic or attenuated strains of Salmonella. Examples of suitable microbial antigens include heat-killed bacteria and liposaccharides of bacteria commonly present in food, e.g., *E. coli* liposaccharides. However, the invention also comprehends explicit exclusion of one or more microbial antigens, including those abovementioned.

Synthetic antigens include any non-toxic substance or toxic substance at low non-toxic dosages which can stimulate a detectable immune response. As used herein synthetic antigens can be synthetic polypeptides, synthetic peptides (e.g., homopolymers, statistical or alternating copolymers, block polymers and graft copolymers, with antigenic determinants for stimulating an immune response, synthetic oligosaccharides or polysaccharides and synthetic haptens. Synthetic antigens include compounds such as 4-hydroxy-3-iodo-nitrophenyl acetic acid (NIP) 2,4-dinitrophenyl (DNP) sulfonate and the like (e.g., see Uanne et al. 1984 *Textbook of Immunology*, Williams and Wilkins, USA).

In some cases a single antigen can be used, however, in other cases several ingestible antigens are preferred. For example several ingestible antigens can be derived from a single food source such as soy, consisting of a mixture of proteins, carbohydrates and other potentially antigenic substances. Accordingly, the methods of the present invention are not limited to immunization of a human or an animal with a single isolated antigen but can be practiced by using a mixture of ingestible antigens obtained from convenient food sources. Preferred mixtures of ingestible antigens are foods commonly consumed by the animal, for example, soy, corn, barley, oats, wheat, sorghum, meat meal, blood meal, egg power, fish meal, milk powder, and whey powder are frequently consumed by farm animals. An especially preferred source for soy or corn antigens is a water soluble extract of soy or corn.

Moreover, the present invention contemplates using several sources of a given food type in a mixture of ingestible antigens. This is done because a given food type obtained from, for example a plant, can have different antigenic properties depending upon the climactic conditions and regions of the world in which the plant was grown. In particular, the present invention contemplates utilizing a mixture of different sources of a single plant product as an ingestible antigen. Plant products which can have variable antigenic properties depending upon the region of the world in which they were grown include, for example, soy, corn, sorghum, wheat, barley and the like.

Any of the foregoing ingestible antigens can be coupled to a carrier. In particular, small antigens like some synthetic antigens and haptens can be used in the present methods when coupled to a carrier. Moreover, any carrier protein known in the art is contemplated by the present invention. Preferred carrier proteins include ovalbumin, bovine serum albumin (BSA), keyhole limpet hemocyanin and the like.

Coupling of an ingestible antigen to a carrier is done by art recognized procedures. For example, such methods are provided in Harlow et al., 1988, *Antibodies: A Laboratory*

*Manual*, Cold Spring Harbor Laboratory. Small antigens can be coupled to carrier proteins using coupling agents like glutaraldehyde, m-maleimidobenzoyl-N-hydroxysuccinimide, bis(sulfosuccinimidyl)-suberate, dimethyl suberimidate, carbodimide, bis-diazobenzidine and others (Harlow et al. 1988).

As discussed in more detail below, the selection of an ingestible antigen depends upon the type of human or animal to be immunized, the immunological history and diet of the human or the animal, and the availability and expense of an ingestible antigen. For example, ingestible antigens for farm animals are generally inexpensive antigens commonly present in feed given the animal especially a fattening fodder feed. However, more expensive, less c ommonly available an t igens can be used for humans and valuable domesticated animals like horses, cats and dogs. Suitable antigens for humans and valuable domesticated animals can include synthetic antigens and microbial antigens as well as unusual plant or animal antigens.

The improved digestion and metabolism of the protein used as an antigen (and of all proteins in the food) depends on the pancreatic enzymes.

This phenomenon can be explained by the fact that the whole gastroenteropancreatic cascade can be immunologically stimulated and, that the cascade:

starts with the gastrin release, followed by the production of acid and mucus, which finally leads to a secretin release with all of its effects.

The discovery of the immunological mechanism for stimulation of the digestive functions represents a new and important contribution for effective control of the digestion; and therefore, provides processes and products for treating or preventing gastrointestinal disorders such as ulcers, as well as for increasing the growth rate or use of food, or for increasing resistance.

An improved feed or food utilization is of maximum importance for animals and humans with a similarly functioning gastrointestinal system, which reacts similarly to the immunological mechanism (gastric cascade) discovered according to the invention.

An outstanding characteristic of the mechanism discovered, on which the invention is based, is the greatly increased digestive capacity through the induction of, primarily, gastric and, in particular, pancreatic secretion.

If small quantities of the antigen against which the animal had been immunized pass into the stomach, these represent a very strong stimulus of gastrointestinal functions. Gastrin and secretin are then released, and the gastric and pancreatic secretion increases. These processes show that small quantities of, for example, a protein in animals immunized against this induce a large increase in digestive capacity.

A decisive factor for the stimulation of the digestion through these immunological mechanisms is not the quantity of food ingested, but the composition of the food. The food must, for example, contain the protein that the stomach can recognize immunologically. This immunological stimulus is even greater than that triggered by the vagus nerve, hormones, or dilation of the stomach. These discoveries by the inventors regarding the immunological mechanism are the scientific basis of the growth promotion and the improvement of the feed and food utilization.

The treatment consequently includes the use of a naturally occurring or synthetic substance, which is either already present in the feed or in human food or can be added, provided that the animal or human is sensitized against this special substance. An oral sensitization takes place predominantly only in a newborn or premature offspring. The treatment consists of administering a biological (i.e., naturally occurring) or synthetic substance (or hapten), against which the organism is immunized, in the feed or food, in the drinking water or other fluids, in solid or liquid form as a tablet, bolus as granules, or in juices, syrup, or molasses or sauces. In addition, the material can be added alone or in combination with other substances or foods already tested or generally recognized as safe that are used routinely for similar or other health purposes or the like.

The quantity of biologically active additive, for example, protein or hapten, as antigen that is required depends on factors, the consideration of which, from this disclosure, are within the ambit of the skilled artisan and do not require undue experimentation. These factors include the:

composition of the feed or food, species, age, sex, and breeding of treated individuals or populations, dose and duration of the immunization.

The following empirical dose is given as a guideline:

1 gram of protein in 100 grams of liquid feed for intragastric stimulation. However, determination of the dose can be readily determined from this disclosure, by the skilled artisan, without undue experimentation.

There are groups of biological and synthetic substances, and also products of activated cells, that have a stimulating or suppressive effect on the immune system. These agents act via T-lymphocytes, B-lymphocytes, macrophages, or natural killer cells. The invention is, however, not restricted to agents already known. The agents can be administered alone or in combination with those also disclosed.

Some agents of this type have already received successful clinical use, particularly the immunostimulating agents:

BCG in mastocarcinomas, melanomas, lymphosarcomas, and bronchial carcinomas;

Bestatin in gastric carcinomas and mastocarcinomas;

Interferons in hepatitis-B, herpes zoster and cytomegalic disease;

Thymus hormones in immunodeficiencies; the immunosuppressive agent;

Cyclosporin, frequently in organ transplants. (Other agents of this type have been tested at least in vitro.)

The presence of antibodies from immunizations is a requirement for the effectiveness of the intragastric antigen administration.

According to the present invention humans or animals are immunized either orally or parenterally. The first immunization is preferably parenteral and parenteral immunization is preferred for subsequent booster immunizations. However very young humans or animals can also be immunized orally since young animals appear to have a capacity for absorption of antigenic substances through the gastrointestinal wall. For example, newly hatched fish are preferably immunized orally by introduction of an ingestible antigen into the water in which these hatchlings swim.

Parenteral immunization can be by any non-oral route including for example by subcutaneous, intramuscular, intradermal or intraperitoneal injection. Parenteral immunization via aerosol applied to the nose or bronchial system is also contemplated by the present invention. Preferably, parenteral immunization is done by intramuscular, subcutaneous, intraperitoneal or intradermal injection.

When a human or an animal is immunized by intramuscular, subcutaneous or intradermal injection the antigen can be mixed with an adjuvant prior to injection. Any type of adjuvant known in the art which is approved by the Food and Drug Administration or the U.S. Department of Agriculture can be used in the present invention. Suitable antigens include for example, Freund's or aluminum hydroxide adjuvants (see, for example, Harlow et al.). It is preferred that humans and animals, particularly food producing animals, be immunized without the use of an adjuvant.

If convenient, ingestible antigens can be incorporated into, and given at the same time, as other injections or immunizations, or when animals are handled routinely, e.g., at weaning or upon release from the nursery. For example, young humans or animals are frequently immunized against diseases or given injections of vitamins during early weeks of life and the present ingestible antigens may be administered therewith.

Moreover, the present invention contemplates using a depot or long term release, preparation of antigen to release antigen either periodically or continuously. When a depot preparation is used it is preferred that antigen be released periodically.

In a preferred embodiment, the present invention is directed to a kit for immunization of humans or animals, either parenterally or orally. A compartmentalized kit for oral or parenteral immunization of a human or an animal, according to the present invention, has at least one container containing an immune-effective amount of an ingestible antigen. It is preferred that the ingestible antigen be sterile. Moreover, kits may also include syringes and needles, as needed for parenteral immunization and an additional container with sufficient ingestible antigen to permit subsequent booster immunizations. If a kit is designed for immunization of several humans, dogs, cats, horses and the like, it is preferred that ingestible antigen be packaged into several containers, each container having sufficient antigen for only one immunization, i.e., a single dosage. However, if a kit is designed for immunization of many farm animals simultaneously, for example piglets at weaning, multi-dosage containers are preferred, i.e., multi-entry vials containing up to 100 dosages of antigen.

For example, if a kit is to be used for immunization of farm animals, preferred antigens such as whey, soy, corn or sorghum can be provided in single-entry or multi-entry vials. Such containers or vials may contain a concentrated solution of sweet or sour whey having about 0.1% to about 20%, and preferably about 10%, protein content. Similarly, kit containers having about 1 to 100 mg/ml, and preferably about 10 mg/ml, soy, corn or sorghum proteins, or mixtures thereof, can be used for immunization of farm animals.

Immunizations can be given at 1 week to 6 month intervals. However, it is preferred that immunizations be given at 2 week to 2 month intervals. Moreover, additional booster injections can be given at various intervals, preferably semi-annually, annually or in 1 to 5 year intervals.

Typically the human or the animal is immunized more than once to elicit an immune response before oral reintroduction of the antigen. It is preferred that the animal be immunized 2 to 4 times with the ingestible antigen.

An immunizing effective amount of ingestible antigen is that dosage sufficient to elicit a detectable immune response. Immunizing dosages range from about 0.01 $\mu$g to about 10 g ingestible antigen per kg body weight and depend on the route of administration. For example, immunizing effective amounts of antigen administered orally are typically about 10 to 100 times the immunizing effective amounts of antigen administered parenterally. Of course, from this disclosure, the skilled artisan can ascertain a suitable dosage, without undue experimentation.

An immune response generated during the initial immunization can be detected, if necessary, as an observable amount of antibodies, reactive with the ingestible antigen, and typically present within the animal's bloodstream or at the mucus membrane of the gastrointestinal tract within one week to six months after the series of immunizations. However, antibodies need not be detectable within the animal's bloodstream at the time of orally reintroducing the ingestible antigen.

Antibodies can be detected by any procedure known in the art including, for example, immunoprecipitation, immunosorbent and immunoelectrophoretic procedures, radioimmunoassays, and enzyme-linked immunosorbent assays. Moreover, such procedures can utilize an antigen or second antibody covalently attached to a label or reporter molecule, for example, a radioisotope, fluorochrome or an enzyme capable of generating a colored, luminescent or fluorescent product. Immunoprecipitation procedures including flocculation, gel immunodiffusion and rocket immunoelectrophoresis are preferred. Gel immunodiffusion procedures are especially preferred for observing an immune response. Harlow et al., for example, provides detailed protocols for immunological detection techniques.

An orally-induced immune reaction can also be observed within the gastric mucosa by detecting mucosa bound antibodies by the above-identified procedures. In particular, biopsy specimens of stomach wall tissue or gastric tissues obtained after necropsy can be tested for an immune reaction by histochemical procedures using antibodies with a detectable label, e.g., a fluorochrome or a radioisotope. Moreover, according to the present invention an immune reaction within the gastric mucosa can be observed by detecting an increase in gastrin, somatostatin or secretin levels in the bloodstream.

According to the present invention orally reintroducing the ingestible antigen refers to feeding the antigen to, or placing the antibody in the stomach of the human or the animal. This can be done by use of a feeding tube or other means of oral administration such as injection into the stomach or intestine. However, a preferred method of orally reintroducing is feeding the ingestible antigen to the human or the animal.

The ingestible antigen is preferably orally reintroduced at most feeding or meal times. In some cases the ingestible antigen is orally reintroduced at irregular intervals, for example, at the same time the human or the animal is exposed to a food type which the human or the animal has previously had difficulty digesting, or when the human or the animal is suffering from a gastrointestinal disease.

The amount of ingestible antigen orally reintroduced can depend on the type and expense of the antigen. For example, low amounts of synthetic antigens are generally present in the orally introduced material because of the expense of many synthetic antigens. The variety of the animal's diet also has an impact on the choice of an amount of ingestible antigen to orally reintroduce. For example, some farm animals are fed a simple diet consisting mainly of a mixture of grains and hay or grass; these animals can receive high amounts of an ingestible antigen commonly present in feed such as corn, sorghum or soy. In contrast, adult humans eat a large variety of foods and, in this case, the ingestible antigen is generally orally reintroduced in small amounts.

The amount of ingestible antigen orally reintroduced can range from about 0.001% to 100% of the orally reintroduced material. In some cases it is preferred that the orally reintroduced ingestible antigen be present initially in small amounts, for example 0.001% to 1.0% of the orally introduced material. Increasing amounts of the ingestible antigen can be orally reintroduced with time, for example over a period ranging from about one week to about six months.

An ingestible antigen can be orally reintroduced in feed, food, drinking water, juices, and as a beverage or fluid. Moreover, an ingestible antigen can be orally reintroduced as a solid, liquid, dressing, syrup, an oral drench, an oral paste, in a capsule or a tablet, especially a chewable tablet.

As used herein, digestion is the normal, healthy process of breaking down and absorbing substances within the gastrointestinal tract of the human or the animal. The process of digestion includes a release of acids, enzymes mucus and digestion regulatory factors into, and an increase in blood flow to, the gastrointestinal tract. Early digestive events include an endocrine release of gastrin and an exocrine secretion of mucus, a release of digestive enzymes and acids, as well as an increase in blood flow within the gastrointestinal tract. Later digestive events include a termination of digestion resulting in diminished gastric acid and digestive enzyme secretion into the lumen of the gastrointestinal tract.

According to the present invention, immunologically stimulating digestion is an initiation of digestive processes occurring as a result of ingestible-antigen immune recognition and stimulation of an immune reaction within the human's or the animal's gastrointestinal tract, particularly within the gastric membrane. This immune reaction can stimulate an entire cascade of digestive events including an increase in blood flow, and a release of acids, enzymes, mucus and digestion regulatory factors within the gastrointestinal tract.

Digestion can be stimulated immunologically by orally reintroducing an ingestible antigen to which the human or the animal has been previously immunized. Immune cells within the human's or the animal's gastrointestinal tract recognize the antigen and communicate with gastrointestinal and non-gastrointestinal cells capable of stimulating blood flow, production of mucus, and release of digestion regulatory factors. Communication between immune cells and other cells can occur by direct or indirect contact of the two cell types or by release of a diffusible substance that acts as a messenger between the two cell types.

Immunologically stimulated digestion can occur in the cephalic, gastric or intestinal phase of digestion. While the present methods are preferably applied to the stomach or gastric phase, immunological stimulation of the intestines can also influence digestion in the intestine. The secretion of acid and pepsin is stimulated to the greatest extent in the gastric phase. During this phase, the antral hormone gastrin is released as the most important stimulus for acid secretion. Acid secretion is necessary for denaturation of the proteins and their degradation, and is also the first infection barrier. The acid, which passes through the pylorus into the duodenal bulb, leads to the release of secretin and also, to a small extent, of cholecystokinin. Secretin strongly stimulates the aqueous components of the pancreatic secretion and thus flushes out the pancreatic enzymes. Through these mechanisms, the whole cascade of digestion is initiated.

A key hormone in the gastric phase of digestion and, consequently, for induction of the digestive processes in the gastrointestinal tract is gastrin. Although this is released through neurogenic, mechanical, and hormonal stimuli, this release is, however, decisively dependent on the individual food components passing into the stomach. Proteins and peptides are the important substances in the food that release gastrin.

FIG. 1 schematically depicts the regulation of antigen stimulated gastrin release. An ingestible antigen is recognized by antigen presenting cells and may stimulate mast cells as well as T-lymphocytes among others. T-cell products gamma interferon (γ-IFN) and interleukin 2 (IL-2) cause release of gastrin which, in turn, stimulates histamine. Mast cell products histamine, leukotriene C4 ($LTC_4$), and prostaglandine $E_2$ ($PGE_2$) can inhibit gastrin release by negative feedback. The vagus nerve may also influence T-cell systems and the antigen presenting cells.

The present invention starts from the finding that, with each meal, the mucosa of the stomach comes into contact with substances that could show immunobiological activity as antigens in the gastrointestinal tract.

Immunizing dosages and dosage regimens to produce an immune response, as well as orally reintroduced dosages sufficient to stimulate an immune reaction and thereby digestion and its associated processes, are readily determined by one of ordinary skill in the art. The present invention provides the following embodiments as guidelines.

In a preferred embodiment, young domestic farm animals are immunized with an ingestible antigen, or antigen(s), which are later commonly present in the feed given the animals. Immunization is preferably done prior to any immunological exposure of the animal to that ingestible antigen.

Preferred ingestible antigens for farm animals are common, inexpensive substances which create no residues harmful to humans in meat, blood, milk or eggs. Examples of some preferred antigens are soy, corn and sorghum proteins and whey. Either native, sweet or sour whey can be used as a mixture or as a source of ingestible antigens. Soy, corn and sorghum proteins or combinations thereof, are especially preferred ingestible antigens for immunization of farm animals.

In a preferred embodiment, a liquid concentrate or a dried powder of whey ingestible antigens can be prepared as a 1% to 20% protein solution and used to initially immunize animals by intramuscular, subcutaneous or intraperitoneal injection. It is preferred that the same source of whey proteins, i.e. either liquid or dry whey, used for initial immunization also be used for oral re-introduction since the antigenic properties of whey can change upon drying, particularly upon heat drying. Therefore, if a cold-concentrated liquid whey solution is used for initial immunization it is preferred that liquid whey, rather than dried whey or a heat-treated liquid whey, be orally reintroduced. Moreover, if a solution of dried whey proteins is used for initial immunization, then dried whey is preferably orally reintroduced as part of the feed, providing for example, between 1% to 20% of the protein content of the diet.

Soy ingestible antigens can be prepared from commercially available sources of soy such as toasted soy flour containing or example 44%, 48% or greater than 90% protein (i.e. Soy 44, Soy 48 or Soy protein concentrate). Similarly, commercially available sources of corn, preferably corn flour, can be used to prepare corn ingestible antigens.

Soy, sorghum or corn flour can be water extracted, preferably at room temperature, and undissolved material can be removed by centrifugation. Water extracted soy, sorghum or corn containing 1–100 mg/ml protein and preferably about 10 mg/ml protein is preferably sterilized by filter sterilization and then about 1–5 ml is used for immunization. Mixtures of whey, soy, sorghum and corn ingestible antigens can also be used for immunization. Mixtures of soy, sorghum and corn are preferred. The proportion of whey, soy, sorghum and corn antigens used for immunization is preferably about the same as the proportion of those antigens in the feed which is orally reintroduced.

Preferred methods for immunization and oral reintroduction of ingestible antigens in several types of animals are provided hereinbelow.

For example, preferred ingestible antigens for piglets are corn, whey, sorghum, soy or mixtures thereof. An especially preferred ingestible antigen for piglets is soy. Moreover, piglets can be immunized intramuscularly or subcutaneously, preferably about two to three weeks after birth, with subsequent injections at about two to four week intervals and an additional injection shortly before changing to a fattening feed containing the ingestible antigen.

Piglets can, for example, be immunized without the addition of adjuvant in the second or third week after birth with about 1–2 ml of a 3% to 9% whey solution. Alternatively, piglets can be immunized with 1–2 ml of a 150 mg/ml soluble soy, corn or soy/corn solution without adjuvant. One to three additional immunizations of such ingestible antigens can be given at about 14–21 day intervals. When changed to a fattening fodder pigs can be given 3 to 6% whey protein in drinking water or soy-, corn- or soy/corn-based feed to orally reintroduce the respective antigens during the entire fattening period.

According to the present invention calves can also be immunized with ingestible antigen in the early weeks of life to promote growth and nutrient uptake and to prevent gastrointestinal disease later in life. Preferably, calves are immunized by intramuscular or subcutaneous injection within about 4 weeks after birth, with a second injection at about 5 to 7 weeks and a third injection in about the eighth to tenth week or when the calf is changed to a high-energy food. The ingestible antigen can be incorporated into the high-energy food or into the drinking water at about 8–10 weeks to optimize digestion and prevent gastrointestinal disorder.

The main constituents of a high energy food for cattle and other ruminants includes corn, wheat, soy, barley, sorghum, silage and hay. These constituents can change depending upon the nutritional requirements of the animal. An ingestible antigen or antigens for calves can be selected from these constituents and used in an immunizing effective amount of from about 0.01 $\mu$g to about 1 g per kg body weight. Preferably, about 0.1 g ingestible antiaen per kg body weight is used for calves. The ingestible antigen can then be present as a constituent of the feed later given the calves.

Horses can also, according to the present invention, be immunized to increase nutrient uptake and growth and to prevent gastrointestinal disorders. Some ingestible antigens for horses include whey, soy, oats or any substance commonly ingested by horses. Moreover, horses can be immunized with antigens which are not commonly present in their feed, e.g., synthetic antigens and some plant antigens. Immunization is preferably intramuscular or subcutaneous. Young foals (3 to 6 months) and mature horses having ulcers, colic or other gastrointestinal diseases can be immunized two to four times at four to eight week intervals over a period of six to twelve months. Annual or semi-annual booster injections may be used thereafter. After the initial series of immunizations the ingestible antigen can be incorporated into the food or water given the horse.

Domestic poultry can also be immunized with an ingestible antigen as provided by the present invention. For example, major food sources for breeding of chickens, turkeys, geese, ducks and related poultry include grains, fish meal, soy and ground peanuts. An ingestible antigen or antigens can be selected from among these food substances and used for parenteral immunization on about the first day after hatching. Later, at about 1 week after hatching, the ingestible antigen can be incorporated into the food or drinking water.

In commercial hatcheries for trout, catfish, salmon and other commercially-produced fish, freshly hatched baby fish are orally immunized repeatedly until they reach fingerling size and are released. Ingestible antigens for baby fish are either suspended in the water of the holding tanks or are incorporated into feed preparations. Preferred ingestible antigens for baby fish are soy, any type of grain, whey powder, milk powder, fish meal, meat meal, blood meal and the like.

According to the present invention humans can also be immunized with an ingestible antigen or antigens. Preferred ingestible antigens for humans include animal antigens from milk, fish, shellfish and others as well as microbial antigens like yeast and the lipopolysaccharides from commonly ingested bacteria. Synthetic antigens and haptens are also preferred ingestible antigens for humans.

Infants are preferably immunized to improve nutrient utilization and growth but can also be immunized to prevent gastrointestinal disease. Moreover, infants can be immunized at the same time as other immunizations (for example, polio, diphtheria-pertussis-tetanus, hemophilus B influenza, and others) are given. Preferred antigens for infants include antigens correlated with colic, diarrhea and other gastrointestinal disease. Preferred antigens for infants also include infant formula, soy products, dairy products, microbial antigens and animal antigens. starting at about 1 to 6 months of life, 2 to 4 immunizations can be given at about one to four month intervals. Booster immunizations can be given subsequently at six month, yearly or longer intervals of time.

Adult humans are preferably immunized to prevent and/or treat gastrointestinal disease, such as ulcers, but can also be immunized to improve nutrient utilization when, for example, traveling, debilitated, malnourished or recuperating from disease. Thus, the invention comprehends products and processes for increasing growth rate or the use of food or, for increasing resistance (especially since nutrient utilization assists in recuperation or growth).

For treatment or prevention of gastrointestinal disease or to improve nutrient utilization, adult humans can be immunized with any ingestible antigen that is routinely ingested by the adult. Alternatively, an ingestible antigen to which the adult has heretofore never been immunologically exposed can be used for immunization and then incorporated into the food or taken with food at mealtime. Use of an antigen to which the adult has not previously been immunologically exposed permits controlled exposure during immunization and oral reintroduction which may optimize immunological stimulation of digestion. If a food type can be identified which the adult has difficulty digesting or which causes gastrointestinal upset, the adult can be immunized with this food type or with antigens extracted from this food type to stimulate digestion of food containing this antigen and prevent gastrointestinal upset.

Preferred ingestible antigens for adult humans suffering from gastrointestinal disease are antigens to which the adult has never been immunologically exposed or to which the adult has difficulty digesting. Preferred ingestible antigens to improve nutrient utilization in adults are routinely ingested antigens, antigens to which the adult has never been immunologically exposed and antigens that have been associated with gastrointestinal diseases like ulcers, diarrhea, constipation and intestinal gas. These preferred antigens can be identified by interviewing the adult to obtain a history of immunological exposure and of food types correlated with gastrointestinal disease.

Immunizing dosages for adult humans are about 1 $\mu$g to about 10 g ingestible antigen per kg body weight. Preferred immunizing dosages are about 0.01 mg to about 1 mg ingestible antigen per kg body weight. However, it is within the ambit of the skilled artisan to determine a suitable dosage from this disclosure, without undue experimentation.

The ingestible antigen can be orally reintroduced into human adults as a portion, for example 0.01% to 50%, of the food or beverage consumed by the adult at mealtime. Moreover, the ingestible antigen can be orally reintroduced as a tablet taken at mealtime, or as granules, dressing or syrup mixed with or applied to food.

According to the present invention gastrointestinal disease can be prevented or treated by immunologically stimulating normal, healthy digestion processes including blood flow, production of mucus and release of digestion regulatory factors within the gastrointestinal tract of a human or an animal. This immunobiologically active, growth-promoting effect promotes the resistance mechanisms in the body, particularly in the case of stress, through specific and non-specifically active defense systems of peripheral lymphatic organs and circulating lymphocytes in the blood and lymph.

For example, blood has bicarbonate, phosphate and protein buffering systems (Guyton, A. C. 1981, *Textbook of Medical Physiology* W. B. Saunders Co. Philadelphia Pa.). Accordingly, increased blood flow within the gastrointestinal tract can regulate acidity of fluids within the gastrointestinal wall by supplying fresh buffering factors and by removing excess acid. This can prevent acidic erosion of gastrointestinal tissues.

Moreover, a release of mucus can coat and protect the walls of the gastrointestinal lumen to prevent, for example, gastric erosions and ulcers.

Diseases of the gastrointestinal tract can occur when digestion is not properly immunologically stimulated or immunologically regulated. For example, when digestion is not properly immunologically stimulated or immunologically regulated, low levels of digestion regulatory factors are released into the blood stream, the discharge of mucus by cells within the gastrointestinal wall is diminished, and there is no increased blood flow to the gastrointestinal tract.

When blood levels of the regulatory factor gastrin are low, digestive enzymes and acids are not properly released into the stomach (Brooks, 1954, Am. J. Dig. Dis. 10: 737–741). Hence, food within the stomach will be poorly digested and many nutrients will remain unabsorbed. Moreover, passage of such undigested food into the intestines can lead to intestinal upset. The presence of poorly digested, nutrient-rich food within the lower intestine can cause an osmotic imbalance or an overgrowth of bacteria, resulting in diarrhea, constipation, painful intestinal gas or other intestinal disorders. Moreover, incomplete digestion of ingested substances can expose the gastrointestinal tract to undesirable substances, e.g., bacteria, viruses and even oncogenic substances, that would have been destroyed by higher levels of acid or digestive enzymes.

In this regard, both humans and animals frequently suffer from gastrointestinal disease when visiting or moving to a new location. Such gastrointestinal disease can result from ingestion of new food antigens that do not adequately immunologically stimulate digestion.

More serious problems develop in infants and young animals which have not had the opportunity to become immunologically exposed to many antigens. Little or no immune response can occur within the stomach walls of such young humans and animals when antigens are introduced in infant formula, baby food or in the food given young animals. As a result, digestion is not properly stimulated and young humans or animals can suffer from malnutrition or from such gastrointestinal problems as colic, ulcers or diarrhea.

Furthermore, the present methods can be applied to prevent exposure of humans and animals to pathogens by naturally stimulating release of digestive enzymes and acids which can kill the pathogens.

Moreover, current procedures of adding organic acids, antibiotics and other substances to animal feed which can have undesirable side effects upon a farm animal or upon a farm animal product, can be replaced by the present methods which have no such side effects. Using this invention, optimum results are achieved in the fattening of animals for meat production, namely, a shortening of the fattening time, with similar feed consumption to reach the final carcass weight.

According to the present invention gastrointestinal disorders like those described above including colic, diarrhea, constipation, intestinal gas, crowding disease, gastric erosions and gastric ulcers can be prevented or treated by immunization with an ingestible antigen and subsequent inclusion of that antigen in the diet.

Many of the experiments conducted to illustrate the present invention utilize in vivo or in vitro animal models to show that nutrient utilization and growth, as well as the prevention or treatment of gastrointestinal diseases, are accomplished by immunologically inducing a response within the gastrointestinal tract of the animal. The value of using animal models for researching medical activities and advances in humans has been recognized for decades. A large body of facts and a remarkable knowledge of interactions on human physiology, biochemistry, microbiology as well as normal and pathological morphology stem from research in animals. "*Principles and Practice of Research*", edited by H. Toidl et al., pp. 149–161, Springer Verlag, 1986. (In "*Principles and Practice of Research*" there is an acknowledgement of the importance of using animal models. For instance, at page 154, "*Principles and Practice of Research*" states: "If you intend to study duodenal ulcer disease, for example, you can look for spontaneous animal models . . . or for an experimentally induced model that was presented as a chemically-induced duodenal ulcer by Szabo").

Animal models are appropriate for use in studying humans and human systems when they exhibit significant similarities and closely resemble the human situation that is to be studied. For example, in Szabo et al., *Am. J. Dig. Dis.* 24:471–474 (1979), a chemically induced duodenal ulcer in rats was found to resemble the human pelvic ulcer disease in morphology as well as sensitivity to therapeutic modulations, and as such, serves as an appropriate model to study the rate of neural, hormonal, and other factors in the etiology and pathogenesis of this disease in humans. Another article, S. Szabo, *Amer. J. Pathology* 93:273–276 (1978), likewise detailed the similarities between cysteamine or proprionitrile induced duodenal ulcers in rats and duodenal ulcers in humans. For example, they have similar pathomorphologic history and are located on the anterior and/or posterior wall frequently penetrating the pancreas. The ulcerations are usually accompanied by increased gastric output and elevated serum gastric levels. Furthermore, there is striking similarity in food sensitive hypergastrinemia in patients and rats with duodenal ulcers.

Accordingly, the testing set forth below demonstrates that the present invention is indeed operative for animals other than those animals employed in in vivo tests, including humans. Moreover, the citations and discussion herein show that the testing set forth herein is art-accepted. Indeed, tests in dogs, rats, and pigs is art-accepted testing to show the utility of the invention in other animals, such as vertebrates, for instance mammals in general, and humans in particular.

Therefore, the present invention provides methods for improving nutrient utilization or growth or resistance in humans and animals and methods for preventing or treating gastrointestinal disease in humans and animals. These methods operate by stimulating normal physiological mechanisms, are inexpensive, have no adverse side-effects, leave no residues harmful to humans in edible animal products, are entirely non-toxic and have demonstrated effectiveness in many species of animals using many types of antigens. Moreover, these methods conserve valuable food resources by improving the conversion of animal feed into an animal product so that more meat or milk products can be obtained using less animal feed. Accordingly, the present methods have enormous potential for alleviating food shortages and gastrointestinal disease throughout the world and for increasing productivity in the animal industry by improving nutrient utilization, growth and disease resistance.

The following non-limiting Examples are given by way of illustration only and are not to be considered a limitation of this invention as many apparent variations of which are possible without departing from the spirit or scope thereof.

EXAMPLE 1

PREVENTION OF EXPERIMENTALLY INDUCED ULCERS BY IMMUNIZATION AGAINST INGESTED ANTIGENS

Male Wistar-Rats (250–350 g) were immunized systemically with NIP-OA (nitrophenyl acetic acid-ovalbumin). To induce ulcers, 1 ml of absolute alcohol was administered into the stomach under ether anesthesia. Fifteen minutes prior to the alcohol application, group I animals (n=12) received NIP coupled to human gamma globulin (HGG) as carrier-protein, while group II animals (n=12) received the carrier protein HGG alone. Non-immunized group III animals (n=6) received NIP-HGG and group IV animals (n=6) received HGG alone, as controls. An hour after administration of alcohol, the animals were killed and the stomachs were removed. Gastric lesions within these stomachs were measured macroscopically by determination of the length of the hemorrhagic lesions.

Figure 2:
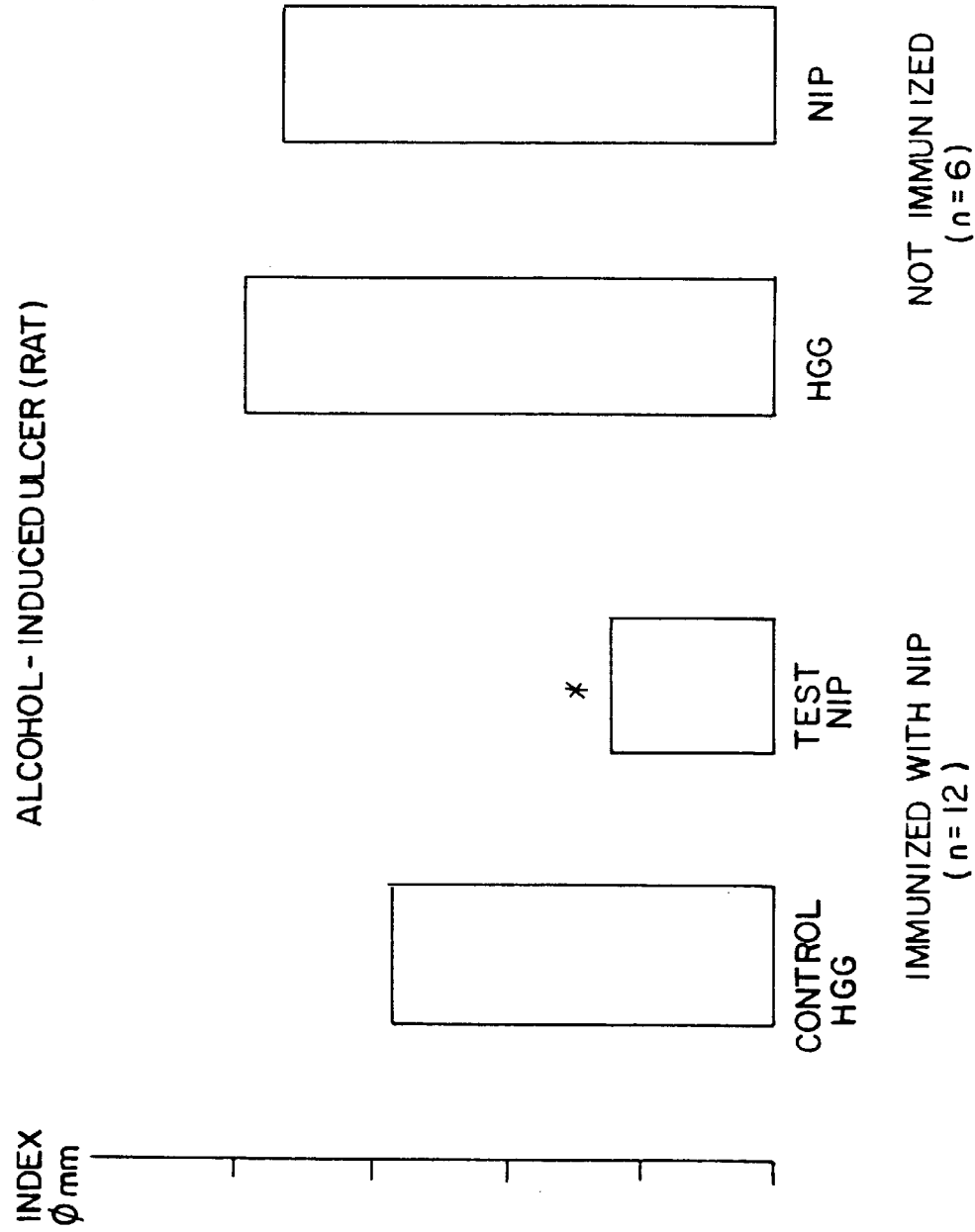
FIG. 2 shows the incidence of ulcers using alcohol induced ulcers in rats as a model system (immunized with NIP, n=12; not immunized, n=6; index ømm)

As depicted in Table 1 and FIG. 2, animals immunized systemically with NIP developed significantly less mucosal lesions after oral NIP-application and subsequent administration of alcohol than all control groups (p=0.02). As illustrated in FIG. 2, rats immunized with nitrophenyl acetic acid (Test NIP) have a significantly lower incidence of ulcers following intragastric application of NIP, than do animals immunized with NIP but intragastrically stimulated with human gamma globulin (HGG) than animals not immunized with NIP.

TABLE 1

| Immunization | Intragastric Administration of | Length of Hemorrhagic Lesions |
|---|---|---|
| I (n = 12) NIP | NIP | 24 p = 0.02 |
| II (n = 12) NIP | HGG | 57 |
| III (n = 6) non-imm. | NIP | 72 |
| IV (n = 6) non-imm. | HGG | 78 |

Therefore, the size of gastric mucosal lesions was significantly diminished by ingestion of an antigen to which an animal was previously immunized.

EXAMPLE 2

PREVENTION OF EXPERIMENTALLY INDUCED ULCERS BY IMMUNIZATION AGAINST INGESTED ANTIGENS

This experimental study demonstrated that prior immunization of rats prevented development of ulcers when the immunized antigen was present in the stomach.

Male Wistar-Rats (250–350 g) were immunized with NIP-OA (nitrophenyl acetic acid-ovalbumin). Ulcers were induced in test and control group rats by inducing SHAY-ulcers through ligation of the pylorus under chlorohydrate anesthesia. Immunized test rats received NIP (coupled to human gamma globulin, HGG) directly into the stomach (test group) immediately after pyloric ligation. Control animals received only HGG carrier protein immediately after pyloric ligation. Another control group consisted of sham operated animals (without pylorus ligation). Eighteen hours after surgery, changes in the stomach wall were investigated macroscopically and microscopically. Gastric lesions including perforations, confluent transmural ulcers and all necroses, were scored if greater than 0.5 cm in diameter.

TABLE 2

| NIP-specifically immunized animals | Intragastric Application of | Proportion Of Animals Showing Lesions | |
|---|---|---|---|
| Test group (n = 24) | NIP-HGG | 7/24 | 29.2% |
| Control group (n = 23) | HGG | 14/23 | 60.9% |
| Sham-operated (n=6 resp. 6) | NIP-HGG resp. HGG | 0/6 resp. 0/6 | |

Figure 3:
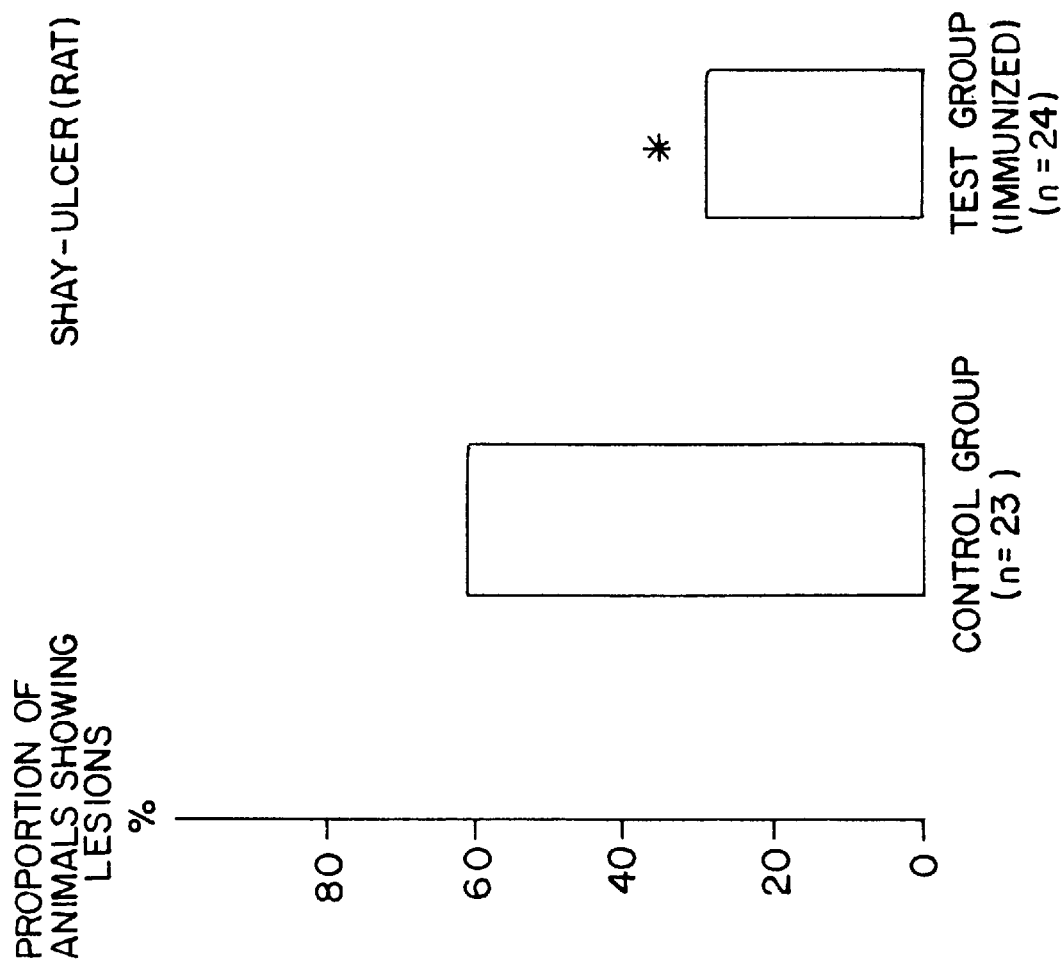
FIG. 3 shows the percentage of animals with gastric lesions induced by the SHAY-ulcer procedure, in animals immunized with nitrophenyl acetic acid-ovalbumin (NIP-OA) (control n=23; test group immunized n=24)

As illustrated in Table 2 and FIG. 3, among animals having pylorus ligations, those previously immunized with NIP had significantly fewer lesions after intragastric application of NIP-HGG (p=0.05) than did those controls receiving only HGG. Sham-operated rats had no mucosal lesions. As depicted in FIG. 3, intragastric application of nitrophenyl acetic acid-human gamma globulin (NIP-HGG) results in significantly lower incidence of peptic ulcers than does intragastric application of HGG alone in control animals.

Therefore, antigen-specific stimulation of gastric functions resulted in a significant reduction of gastric wall lesions in a defined ulcer model (pylorus ligation).

EXAMPLE 3

PREVENTION OF NATURALLY OCCURRING ULCERS BY IMMUNIZATION AND BY IMMUNIZATION AND SUBSEOUENT INGESTION OF AN ANTIBODY

After weaning in the second week of life, piglets are generally fed a coarse grain fodder and then changed over to a very finely ground fattening feed. Such a fattening feed has been documented to be a major cause of ulcerous changes such as hyperkeratoses, erosions and ulcers in the gastric mucosa of pigs (Breukink et al. 1989 Veterinary Record 125: 109–111; Stanton et al. 1989 J. Vet. Internal Med. 3: 235–244; Kowalczyk, T. 1975, Gastric Ulcers. In: *Diseases of Swine* Leman, A. D. and Dunne, H. W., Eds. Fourth Edition, The Iowa State University Press Ames, Iowa). This experiment illustrates that methods of the present invention can be used to prevent or treat such ulcers.

Thirty immunized pigs were used as a test group and thirty non-immunized pigs were used as a control group to illustrate the prophylactic effects of immunization with whey proteins upon the gastral mucosa.

Test group piglets were immunized parenterally in the third week of life and at an interval of 14 days with 2 ml of a 10% whey protein solution without addition of adjuvant. Later, piglets were orally reintroduced to whey using fresh whey instead of drinking water.

After weaning of the piglets in the second week of life, the diet of both test and control piglets was gradually changed from pig breeding feed to coarse grain fodder. At about 10 weeks of life both test and control animals were brought into another pig sty, kept in loose housing boxes and fed very finely ground fattening feed. Also at about 10 weeks, both test and control groups of animals were given fresh whey instead of drinking water for an entire fattening period of about 16 weeks.

Changes of the gastric mucous membrane of pigs in the area of pars proventricularis were evaluated according to pathological criteria as follows:

"O" was used for an intact mucosa;

"+" was used for low grade, flat hyperkeratoses;

"++" was used for moderate hyperkeratoses with pointed serrations; and

"+++" was used for serious changes in the mucus membrane, e.g., erosions.

Table 3 shows the frequency (number and percentage) of pigs having 0 to +++ gastric mucosal ratings after 16 weeks on a diet of very finely ground feed.

TABLE 3

| 0 | + | ++ | +++ | |
|---|---|----|-----|---|
| 6 | 6 | 6 | 8 | control group |
| 21.4% | 21.4% | 21.4% | 28.6% | n = 28 |
| 10 | 7 | 7 | 2 | test group |
| 40% | 28% | 24% | 8% | n = 25 |

Figure 4:
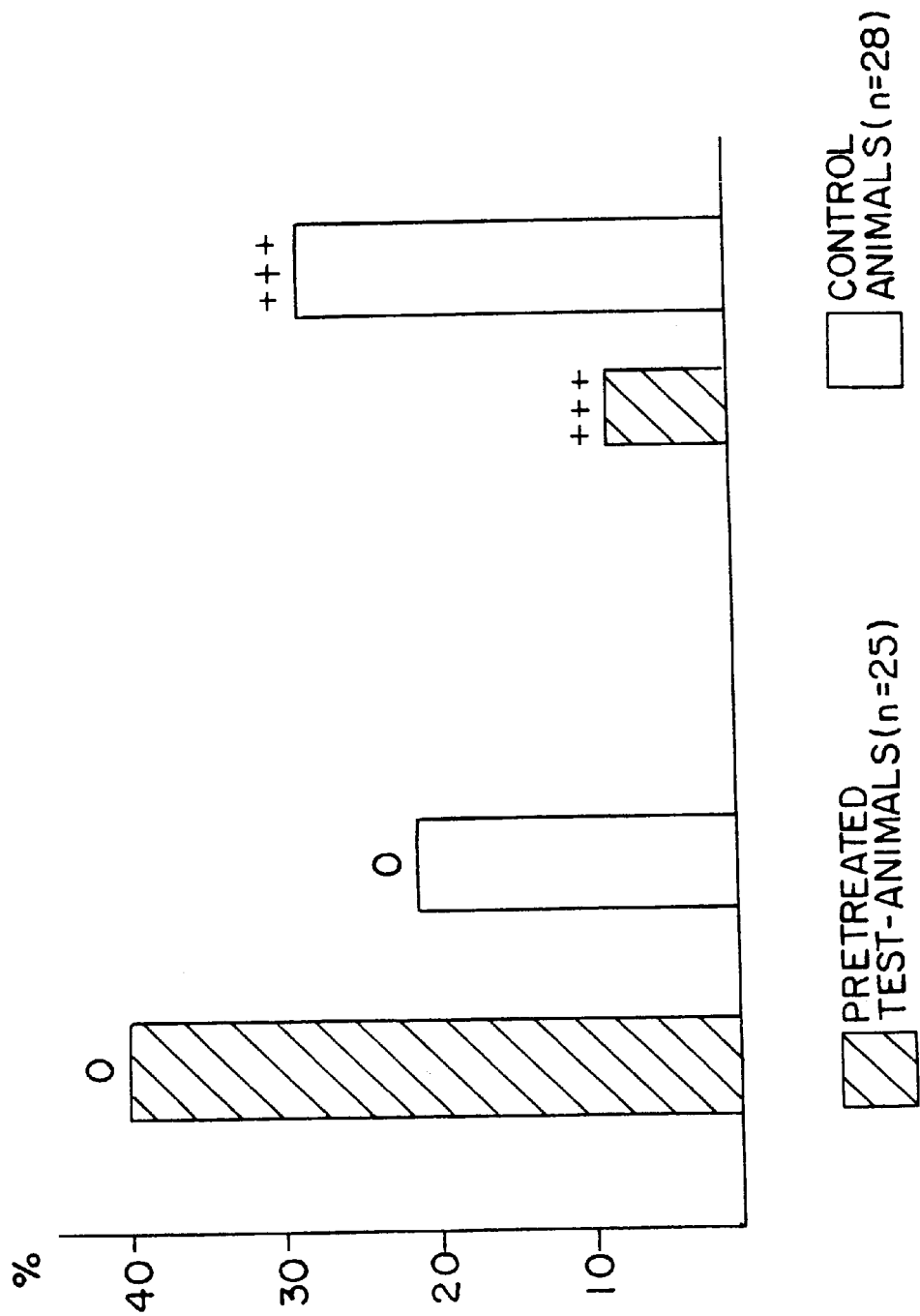
FIG. 4 shows a pathological evaluation of the gastric mucus membrane of pigs in the area of the pars proventricularis after 10 weeks of feeding a very finely ground feed ration and a 6% whey solution as drinking water (pretreated test animals, n=25; control, n–28)(The percentage of non-immunized control animals (open box) and whey-immunized animals (black box) having an intact gastric mucosa (0) is compared to those having severe changes in gastric mucosa (+++) e.g., gastric erosions and ulcers)

FIG. 4 graphically presents the data for pretreated immunized test animals (black box) as compared to non-immunized control animals (white box). The designation "O" is used to indicate the incidence of animals having an intact mucus membrane while "+++" indicates the incidence of serious changes in the mucus membrane, e.g., erosions.

Animals immunized with whey protein were much more likely to have an intact mucous membrane than were animals receiving no immunization. Moreover, serious changes of the mucous membrane, e.g., erosions, (designated as "+++") occurred 70% less frequently in immunized animals than in control non-immunized animals.

EXAMPLE 4

IMMUNIZATION OF CATTLE

Dairy Cows and Bulls

As an antigen, a protein is used which is not present in calf food, especially not in the milk replacer with which the calves are fed after birth. However, the selected antigen should be present in the high-energy food which is given to the calves in about the eighth to tenth week after birth. Ulcerative lesions generally develop during the change to high-energy food, usually at an age of four to ten weeks. These disorders can occur when no immunization of animals is done with antigens present in the high-energy food. The main constitutes of the high energy food for ruminants are mainly corn, wheat, soy, barley, grassilage and hay. These constituents may change according to the degree of intensive breeding. Accordingly, an antigen is chosen from among these constituents, on the basis of availability and the degree of intensive breeding.

The first intramuscular injection of the antigenic substance will be given in the first four weeks after the birth of the calf. A second injection will follow in the sixth week and a third injection at the time when high-energy food will be given in the eighth to tenth week. In the first week after birth the calves receive milk and starter diet. They will receive high-energy food about the eighth to tenth week. Then, at the time of changing to the high-energy food, the antigenic substance will be added to the food and/or drinking water to use or establish the immunological protection of the gastrointestinal tract by the above-described immunological mechanism.

The dose of the antigenic substance should be about 0.1 g antigenic test substance per kg bodyweight by intramuscular application and will be repeated two or three times.

To induce the protective mechanisms, i.e., to improve nutrient utilization and growth of the animal and to prevent and treat gastrointestinal disease, the antigenic substance will then be added to the drinking water in a dose of up to 1 g per 100 ml water. By performing this procedure, ulcerative lesions in the gastrointestinal tract of the calves is prevented or reduced.

Handling of cattle, by these methods, leads to protection against changes of climate, food and transports ("Crowding Disease"), especially within the first weeks after birth. Moreover, frequent disorders or diseases of the gastrointestinal tract, occurring during such environmental changes, especially diseases like diarrhea, may well be prevented by these methods. Diarrhea can also be the cause of other bacterial or viral diseases in the gastrointestinal tract, which may be also prevented if these methods are employed.

Concerning the use of antigenic substances in adult ruminants, the required antigenic substances will be applied in bulls and cows during the period of intensive feeding and high lactation. Thus, common gastric ulcers also may be prevented or reduced in adult animals.

Veal Calves

Veal calves, particularly those raised for white veal production are particularly prone to stomach ulcers. For example, between 30% and 70% of veal calves have ulcers which reduce growth of the animal. Veal calves are predominantly fed soy, cottonseed meal, molasses proteins, milk powder and/or whey powder in a milk replacer diet. Therefore, an ingestible antigen is selected from among these food types. Calves are immunized with about 0.1 mg to 0.1 g of ingestible antigen in the first four weeks of the life and about two more times at 2–4 week intervals. A milk replacer diet is introduced at about 1–4 weeks of life at which time the ingestible antigen can be orally reintroduced.

Veal calves are fed this milk replacer diet during the fattening phase until the calf is slaughtered at about 350 pounds of weight which occurs at about 4–4½ months of age (As a comparison with respect to pigs, see FIGS. 13 and 14 and discussion thereof, below).

EXAMPLE 5

IMMUNIZATION OF ANIMALS WITH A FOOD ANTIGEN IMPROVES NUTRIENT UPTAKE AND GROWTH

A. Experiment 1

In a preliminary pilot experiment concluded under field conditions, piglets after weaning from the mother animals were immunized with whey protein in a pig fattening operation. Thereafter, the animals were given whey, added to the drinking water.

Although all of the animals (n=20) were suffering from an infectious intestinal disease, growth of the animals was hindered by the infection only in the ten untreated control animals. After disappearance of the infection, an even higher growth rate started in the treated animals.

The daily weight gain up to the carcass weight was 675 grams in the treated group and 600 grams in the untreated group.

The feed utilization, i.e., the amount of feed per kilogram required to increase the body weight by one kilogram, was 1:2.45 in the treated group, as compared with 1:3.25 in the controls.

In this pilot study, the daily weight gain improved by +12.5% and the feed utilization by +24%.

These experiences and observations formed the basis for the following experiment:

This double blind experiment was performed over a 25 week period and involved 44 improved German Landrace pigs (22 males and 22 females, divided into four groups of 11 animals each). The piglets were weaned from the mother animals at the age of 28 days. Up to week 10 the animals received commercial, standardized piglet rearing feed. After weaning, the animals were assigned to one of the following groups on a random basis:

Group 1: Parenteral sensitization with whey and individual weighing.

Group 2: Parenteral sensitization with whey and determination of the group weight at the beginning and end of the experiment.

Group 3: No immunization (saline injection) and individual weighing.

Group 4: No immunization (saline injection) and determination of the group weight at the beginning and end of the experiment.

The animals of Groups 1 and 2 were immunized three times, at the age of 4, 7 and 10 weeks, by subcutaneous injection of 1.0 mL of commercial, concentrated milk-protein solution (whey, protein content 10%).

From week 10 on, the animals received a commercial fattening feed of uniform composition and also were given whey in the drinking water. In this way, a continuous enterogastric stimulation between the orally ingested milk protein and the parenterally sensitized gastric mucosa were ensured.

Groups of 11 pigs were housed in a shed with a slatted floor without litter, with liquid feeding twice a day (whey and fattening feed) and free drinking (whey in the drinking water). The amount of feed consumed and amount of whey were determined and recorded electronically.

All animals were weighed as a group at the beginning of the experiment, after 10 weeks, and at the end of the experiment after 15 weeks. In Groups 1 and 3, all animals were also weighed individually, at the end of weeks 3, 5, 7, and 11 of the fattening period. The average weight per animal and group was determined.

All animals were slaughtered after 15 weeks (at the age of approximately 25 weeks) and the meat was classified according to the EC guidelines.

Results

Figure 14:
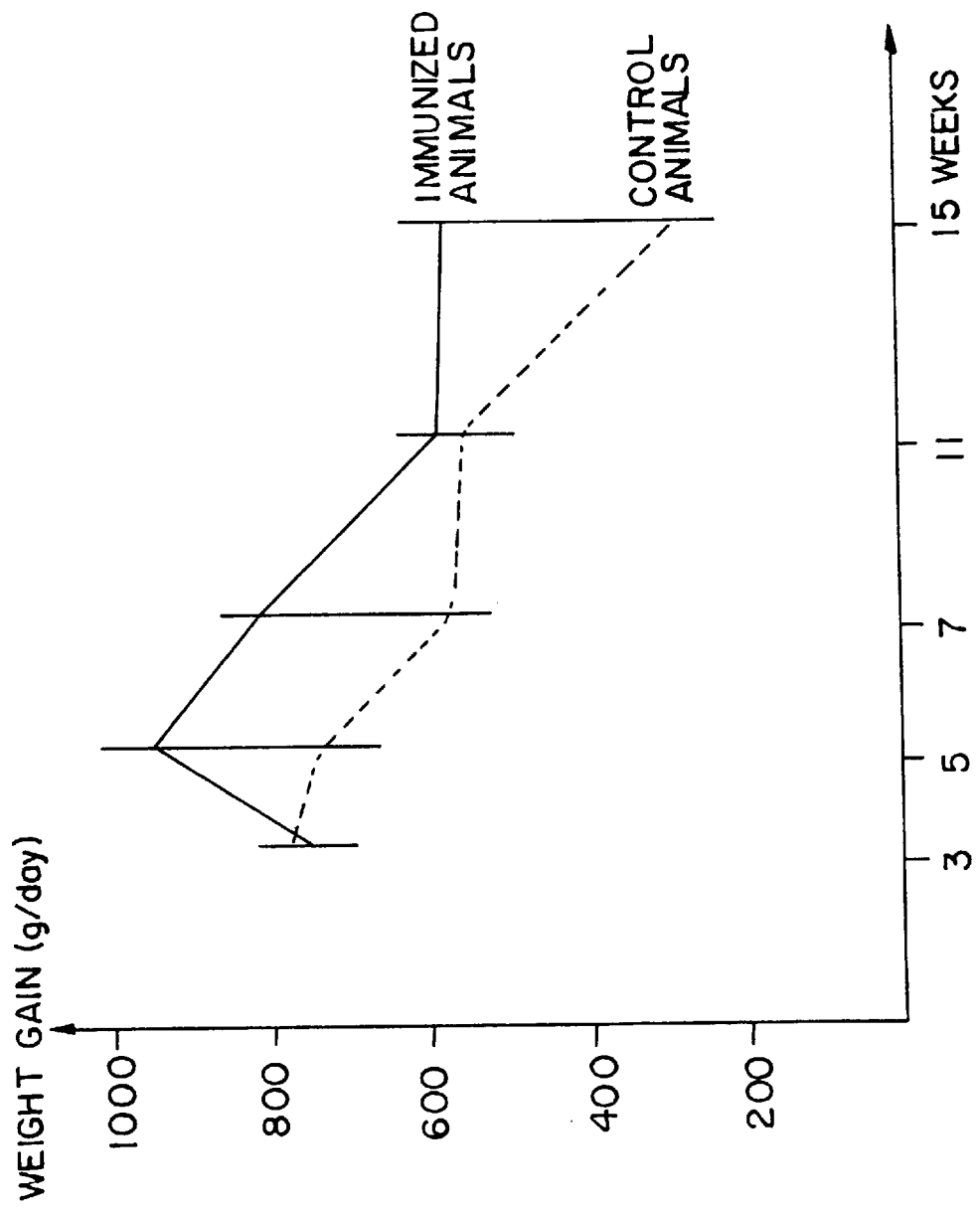
FIG. 14 shows the average daily weight gain in grams by immunized animals (pigs) and control animals (pigs) during the final twelve weeks of fattening (weight gain, g/day vs. weeks)
Figure 15:
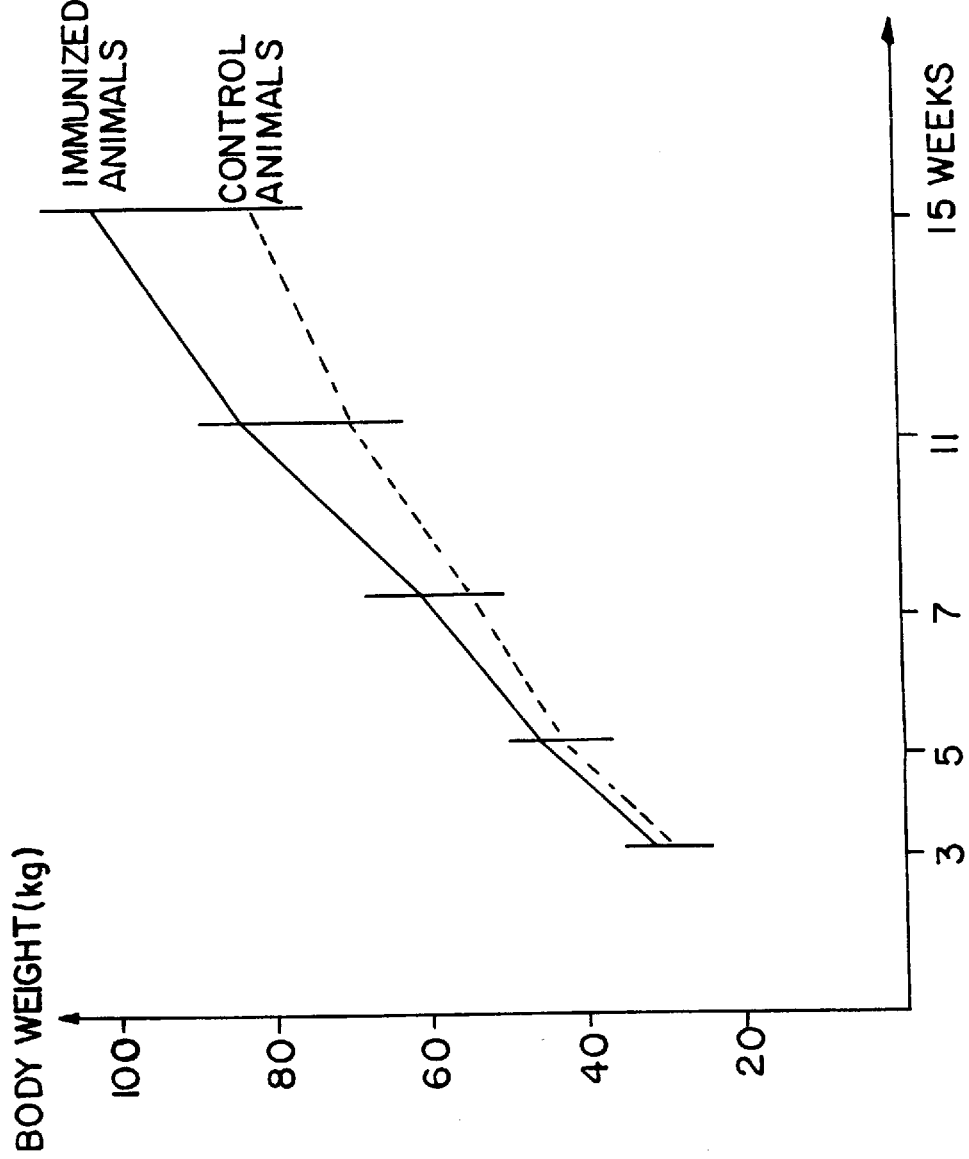
FIG. 15 shows the increase in body weight in kilograms by immunized pigs and control animals during the trial twelve weeks of feeding (body weight, kg vs. weeks)

The daily weight gain, total body weight at the end of the experiment, and weights and feed utilization rates of all groups are shown in Table 4 and FIGS. 14 and 15.

The evaluation of the carcasses animals, independent of the treatment, produced the classification E-1 (excellent) according to the EC guidelines.

The results of the experiment show clearly that, after previous immunization and subsequent enterogastric antigen administration, the feed utilization, and thus the daily weight gain, increased considerably. The live and carcass weight of the immunized animals are therefore increased significantly after 15 weeks, by +16% and +18.5%, respectively. These results correspond to those of the pilot (preliminary experiment) and show clearly that the treatment, i.e., immunization and (subsequent) administration of the antigen with the feed, for animals under otherwise identical conditions, is not only extremely effective with an increase by 30.4% in feed utilization, but is also economically extremely advantageous for the breeder, since the feed consumption for fattening decreases distinctly by 13.5%.

No side effects were found with this treatment.

On the contrary, the pigs in Groups 1 and 2 recovered from a viral infection, which caused diarrhea, more rapidly than the control animals; the daily weight gains, after the infection had been overcome, immediately started to increase again (FIG. 15), but not in the control group.

These results and investigations, which were carried out under field conditions in both experiments, clearly prove that the invention—on the basis of investigations on laboratory animals—can be used successfully in animal production.

TABLE 4

Weight Gain and Feed Utilization in Animals Immunized with Whey and Control Animals (Pigs) During a 15-Week Fattening Period

| Groups and Treatment | n | Weight Gain per Day (g) | Feed Utilization | Feed Consumption (kg) | Live Weight After 15 Weeks (kg) | Carcass Weight (kg) |
|---|---|---|---|---|---|---|
| 1 + 2 Immunized with Whey | 22 | 604 | 2.75 | 175.0 | 97.7[a] | 81.2[a] |
| 3 + 4 Control | 22 | 530 | 3.95 | 202.4 | 84.2[b] | 68.5[b] |
| Difference | | 74 | 1.20 | 27.4 | 13.5 | 12.7 |

TABLE 4-continued

Weight Gain and Feed Utilization in Animals Immunized with Whey and Control Animals (Pigs) During a 15-Week Fattening Period

| Groups and Treatment | n | Weight Gain per Day (g) | Feed Utilization | Feed Consumption (kg) | Live Weight After 15 Weeks (kg) | Carcass Weight (kg) |
|---|---|---|---|---|---|---|
| (%) 1 + 2 vs. 3 + 4 | | (+14) | (+30.4) | (−13.5) | (+16.0) | (+18.5) |

[a]vs. b: $p < 0.05$ (Wilcoxon test for non-parametric distributions)
[b]In the absence of differences within groups 1 + 2 and 3 + 4 in each case, the results have been combined.

B. Experiment 2

After weaning and a change to semi-liquid high energy diet, piglets frequently develop gastrointestinal problems which are exacerbated by stressful living conditions such as an inadequate diet. These experiments illustrate the benefits of preimmunization of an ingestible antigen upon nutrient utilization and growth of pigs under stressful living conditions.

To generate stressful living conditions, pigs were fed twice daily on a marginally adequate maintenance diet. Moreover, all animals were subjected to frequent gastroscopic examinations and gastric wall tissue sample biopsies (at all weighing dates shown in Tables 5 and 6). In addition, animals were subjected to the stress of frequent blood samplings.

Two groups of four nondescript crossbred pigs were maintained on a diet free of soy protein. Group 1 was immunized subcutaneously with finely milled soy 44 (commercial soy meal containing 44% protein) three times at 18 and 14-day intervals. Group 2 was not immunized. Two and a half weeks after the last booster injection all hogs received a diet containing soy 44. After three months, all hogs were slaughtered.

Biopsy samples demonstrated that the stomach epithelium from immunized animals immunologically recognized soy 44 (by tests like those in Example 7).

All eight pigs were finally weighed on Apr. 8, 1991. As illustrated in Tables 5 and 6, immunized animals had a mean weight of 98.1 kg while non-immunized control animals had a mean weight of 90.0 kg. The average daily gain (ADG) between Nov. 20, 1990 and Apr. 8, 1991 was 516.3 g per immunized animal and 456.6 g per non-immunized animal. This is a difference of 13.1% in weight for animals immunized with soy over untreated controls. Therefore, even under stressful conditions not conducive to normal levels of growth, animals immunized with soy grew faster. The economic advantage of immunization with an ingestible antigen followed by routine feeding of that antigen is illustrated by a calculation of the number of additional days nonimmunized animals had to be fed to reach the slaughter weight of immunized animals. In this study that time was approximately 17.7 days.

TABLE 5

Effect of immunization and subsequent feeding of soy of 44 hogs
A. Immunized Animals

| Animal Number | 11/20/90 Soy i.m.* Soy-free feed** | 12/08/90 Soy i.m.* Soy-free feed** | 12/22/90 Soy i.m.* Soy-free feed** | 01/08/91 Soy in feed*** | 01/22/91 Soy in feed*** | 03/07/91 Soy in feed*** | 04/08/91 Soy in feed*** |
|---|---|---|---|---|---|---|---|
| 1 | 26.4 | 34.1 | 49.9 | 55.0 | 67.1 | 85.5 | 101.5 |
| 2 | 18.7 | 26.0 | 37.0 | 42.5 | 55.0 | 71.0 | 92.0 |
| 3 | 25.9 | 35.5 | 46.9 | 51.3 | 65.1 | 79.0 | 92.0 |
| 4 | 26.2 | 35.8 | 50.0 | 56.4 | 68.4 | 86.0 | 101.0 |
| Total | 97.2 | 131.4 | 183.8 | 205.2 | 255.6 | 321.5 | 392.5 |
| Mean: | 24.3 | 32.9 | 46.0 | 51.3 | 63.9 | 80.4 | 98.1 |
| S.D. | 3.7 | 4.6 | 6.1 | 6.2 | 6.1 | 7. | 4.4 |

*Soy i.m. indicates immunization with soy 44 (soy meal containing 44% protein)
**Animals did not receive soy in their diet until January 8, 1991.
***Animal received soy 44 as part of their diet. Animals were fed twice daily.

TABLE 6

Effects of no immunization and subsequent feeding of soy of 44 hogs
B. Non-Immunized Animals

| Animal Number | 11/20/90 Soy-free feed** | 12/08/90 Soy-free feed** | 12/22/90 Soy-free feed** | 01/08/91 Soy in feed*** | 01/22/91 Soy in feed*** | 03/07/91 Soy in feed*** | 04/08/91 Soy in feed*** |
|---|---|---|---|---|---|---|---|
| 8 | 33.5 | 43.0 | 56.2 | 62.0 | 74.4 | 89.0 | 97.0 |
| 7 | 28.7 | 36.5 | 49.8 | 55.4 | 64.6 | 82.0 | 96.5 |

TABLE 6-continued

Effects of no immunization and subsequent feeding of soy of 44 hogs
B. Non-Immunized Animals

| Animal Number | 11/20/90 Soy-free feed** | 12/08/90 Soy-free feed** | 12/22/90 Soy-free feed** | 01/08/91 Soy in feed*** | 01/22/91 Soy in feed*** | 03/07/91 Soy in feed*** | 04/08/91 Soy in feed*** |
| --- | --- | --- | --- | --- | --- | --- | --- |
| 6 | 22.1 | 30.7 | 44.1 | 50.0 | 63.0 | 78.5 | 95.5 |
| 5 | 14.5 | 22.5 | 31.1 | 36.3 | 45.0 | 58.0 | 71.0 |
| Total | 98.8 | 132.7 | 181.2 | 203.7 | 247.0 | 307.5 | 360.0 |
| Mean: | 24.7 | 33.2 | 45.3 | 50.9 | 61.8 | 76.9 | 90.0 |
| S.D. | 8.3 | 8.7 | 10.7 | 10.9 | 12.3 | 13.3 | 12.7 |

**Animals did not receive soy in their diet until January 8, 1991.
**Animal received soy 44 as part of their diet. Animals were fed twice daily.

Three additional independent studies were performed which illustrate the effects of prior immunization and subsequent feeding of an ingestible antigen upon animal growth and nutrient utilization.

Figure 16:
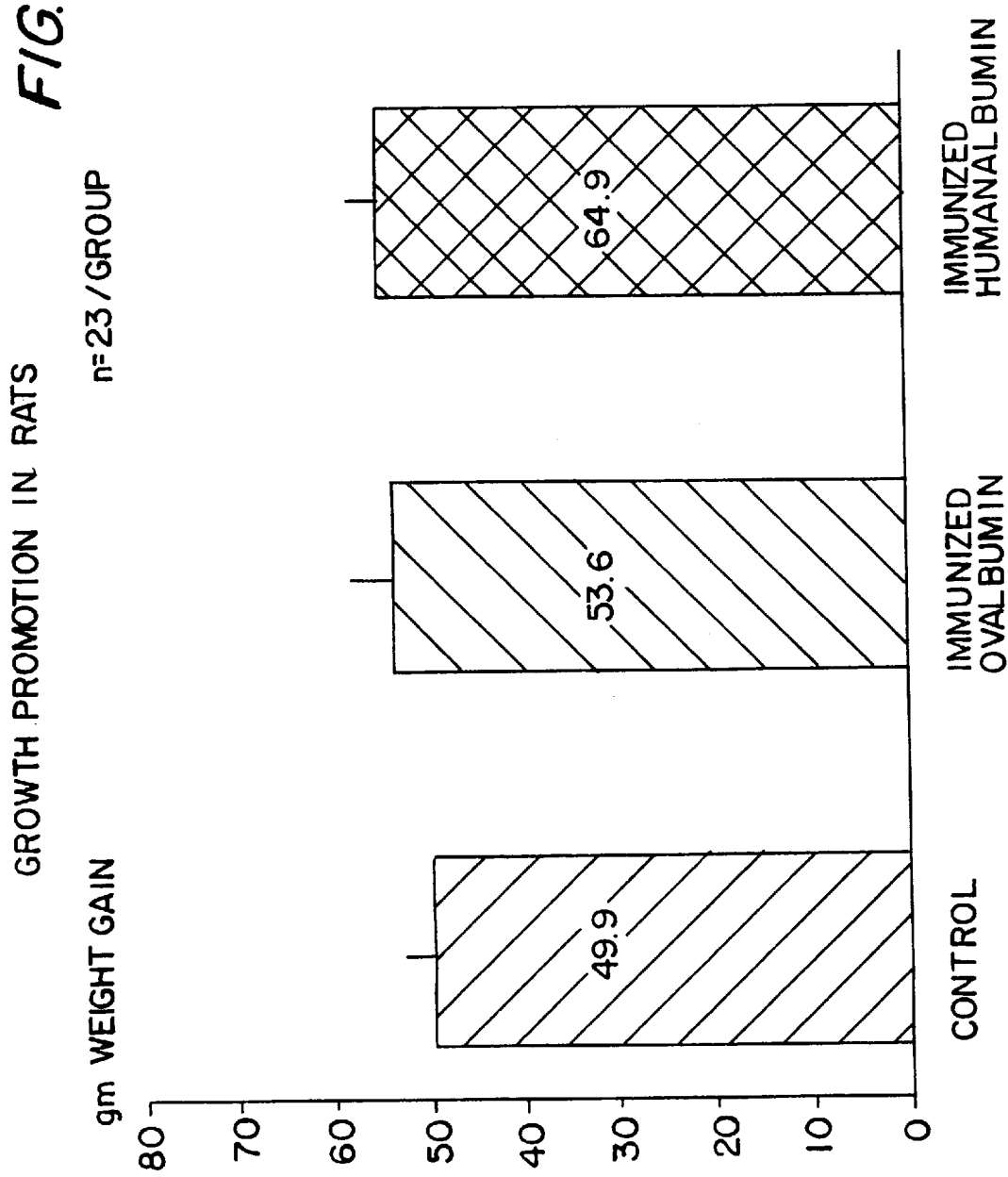
FIG. 16 shows the growth promotion in rats immunized with ovalbumin and human albumin and routinely orally reintroduced to these antigens by incorporation of the antigens into the diet (grams weight gain; n=23/group; control= 49.9, immunized with ovalbumin=53.6, immunized humanalbumin=54.9)

A. Rats were immunized with either ovalbumin or human albumin and routinely orally reintroduced to these antigens by incorporation of the antigens into the diet. In two experiments, nitrogen utilization of immunized animals was 10.35% and 6.8% greater than observed for non-immunized animals. Moreover, the average daily weight gain was 7.4% and 10.0% higher for immunized animals relative to non-immunized animals. FIG. 16 shows the weight gain in grams of rats immunized with both ovalbumin and human albumin as compared to a control group. Growth promotion was clearly shown in those rats who were immunized with either antigen and routinely reintroduced to these antigens by incorporation of the antigen into the diet.

B. Ten hogs were immunized with whey and subsequently fed whey in the diet. As a control ten other hogs were not immunized but received a diet identical to immunized hogs. In immunized hogs, the average daily weight gain and the food conversion rate was 12.5% and 24% higher, respectively, than observed for control animals.

C. In an additional study using 44 hogs (22 males and 22 females) immunized with and then fed whey, the average daily weight gain and food conversion rate was 14% and 30.4% higher compared to non-immunized control animals, respectively.

EXAMPLE 6

IMMUNOLOGICAL STIMULATION AND REGULATION OF DIGESTION

According to the present invention, recognition of ingested antigens by immune cells within the gastrointestinal wall stimulates and regulates digestion. The experiments described below exemplify some of the digestive processes which can be immunologically stimulated and regulated.

A. Experiment 1
Experimental Design

Two groups of dogs (10–15 kg) were used. One group was immunized intramuscularly with a protein foreign to the dog, human gamma globulin (HGG) in Freund's adjuvant. Four weekly injections were given until circulating antibodies were found in the dogs' serum by an Ouchterlony test. All dogs were then anesthetized and 1 g of HGG dissolved in 100 ml water was placed in the dogs' stomachs via a nasogastric tube. During the following hour of investigation, hormones, blood flow, heart volume, blood pressure and blood gases were monitored. Blood flow was measured by a microspheres technique using radiolabeled particles of 15 mm diameter.

Gastrin Release

Blood levels of gastrin were determined as previously described (Teichmann 1983a, Vagale und Immunologische Stimulation gastraler Funktionen. Habilitationsschrift, Ludwig-Maximilians-Universitaet Muenchen; Teichmann et al. 1983b, Gastroenterology 84:1333)

Application of the antigen into the stomach of non-immunized dogs did not stimulate gastrin release. However in immunized dogs there was a highly significant increase of serum gastrin from basal values of 1±0.3 pg/ml to 12±5 pg/ml within 5 min. Gastrin remained elevated for 45 minutes and decreased slowly at 60 minutes.

Specificity of Immunological Stimulation

After intragastric administration of an antigen to which the animals had never been immunologically exposed (human albumin), no release of gastrin was observed.

When the immune response against HGG decreased, at about 8 weeks after the last immunization, there was diminished release of gastrin following intragastric administration of HGG. However, reimmunization with HGG and intragastric administration of HGG led to release of significant levels of gastrin equivalent to levels previously observed.

Comparison of Secretin and Gastrin Release

Secretin and gastrin levels in the blood were measured as described previously (Andress, H. J. 1985, Nahrungs-und Antigen-induzierte gastrointestinale Hormonfreisetzung und Durchblutung vor und nach Vagotomie. Inaugural Dissertation, Ludwig-MaximiliansUniversitaet Muenchen).

Figure 5A:
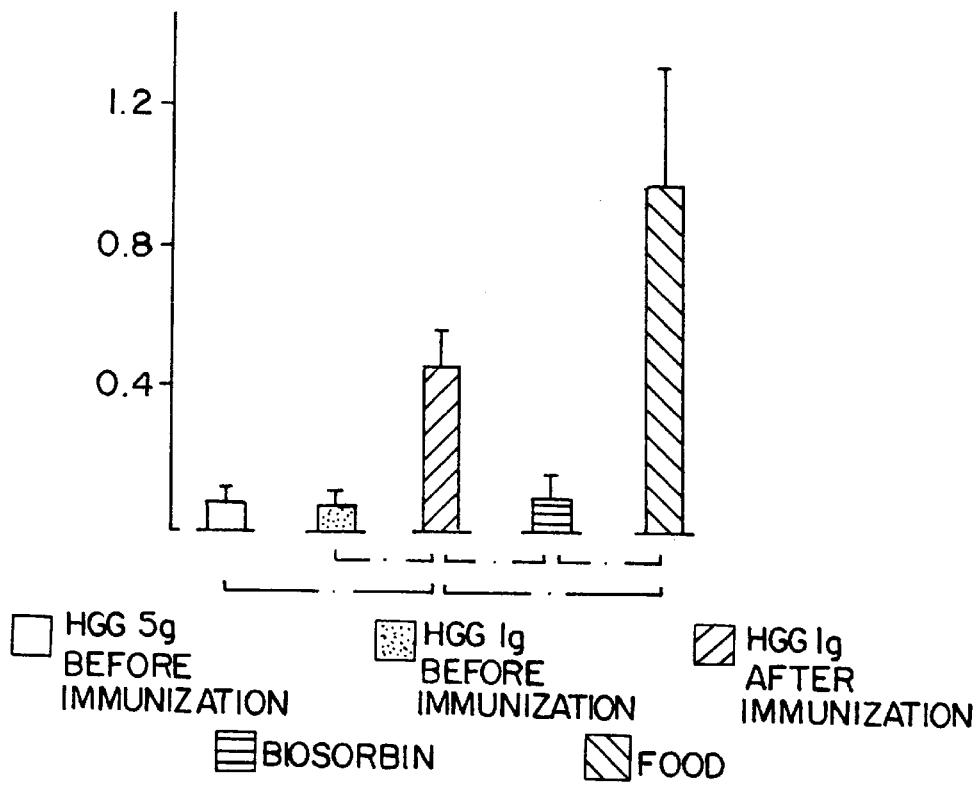
FIGS. 5a and 5b show total gastrin (a) and secretin (b) release in dogs before and after immunization with human gamma globulin (HGG) upon intragastric administration of HGG or ingestible antigens to which the animal is (food) and is not (Biosorbin$^R$) immunologically familiar.

An integrated hormonal response was calculated from gastrin and secretin levels as the concentration released within one hour per ml of serum or plasma. As depicted in FIG. 5a, no release of gastrin was observed before immunization with HGG when 5 g or 1 g of HGG was given intragastrically. However, after immunization with HGG, there was a significant release of gastrin when only 1 g of HGG was given intragastrically. Moreover, 5 g of dog food, with which the dogs were immunologically familiar, caused a significant stimulation of gastrin (FIG. 5a).

A commercially available fluid diet, BIOSORBIN®, with no HGG, caused almost no gastrin or secretin release even though BIOSORBIN® is a complete, nutritionally balanced fluid diet specifically designed to be readily digestible by patients who are unable to swallow food. Moreover, the content of proteins and peptides, on a molar basis, was higher in the BIOSORBIN® than in the HGG solution used in these experiments (FIG. 5a and FIG. 5b).

Figure 5B:
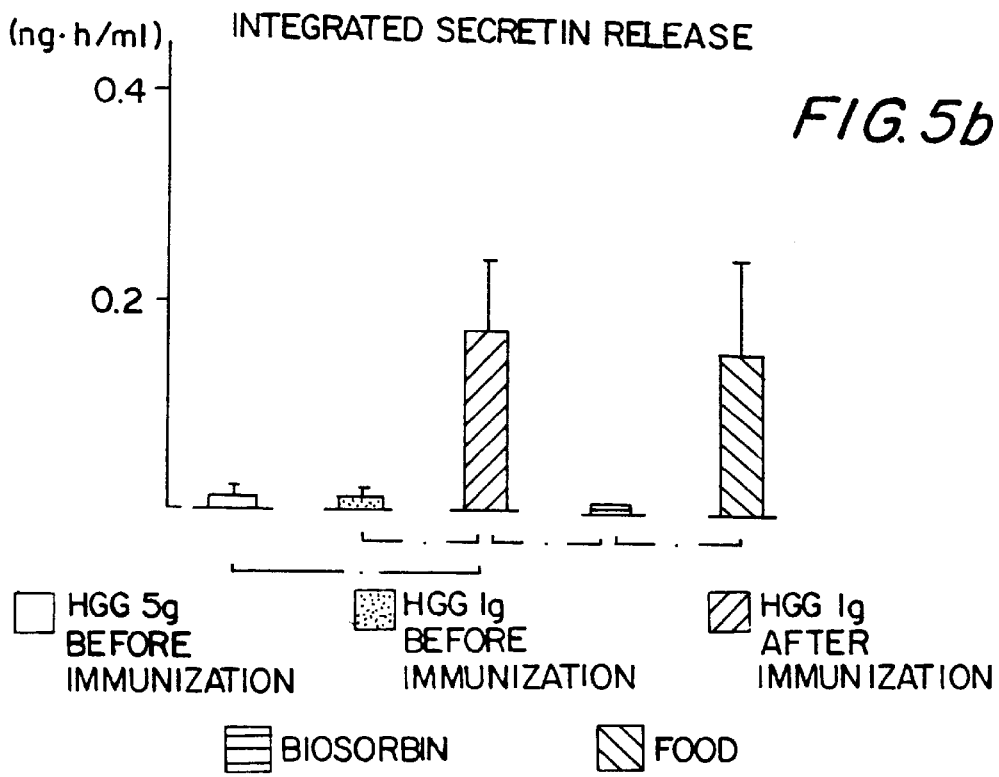

Integrated secretin values were also elevated following intragastric administration of 1 g HGG in immunized dogs (FIG. 5b). This secretin release was as pronounced as that seen after feeding dog food. Note that BIOSORBIN®, which is a nutritionally complete liquid diet specifically designed to be easily digested by patients unable to swallow to food, does not stimulate gastrin or secretin release as well as an antigen (HGG) to which animals are immunologically familiar.

Mucus Secretion

Figure 6:
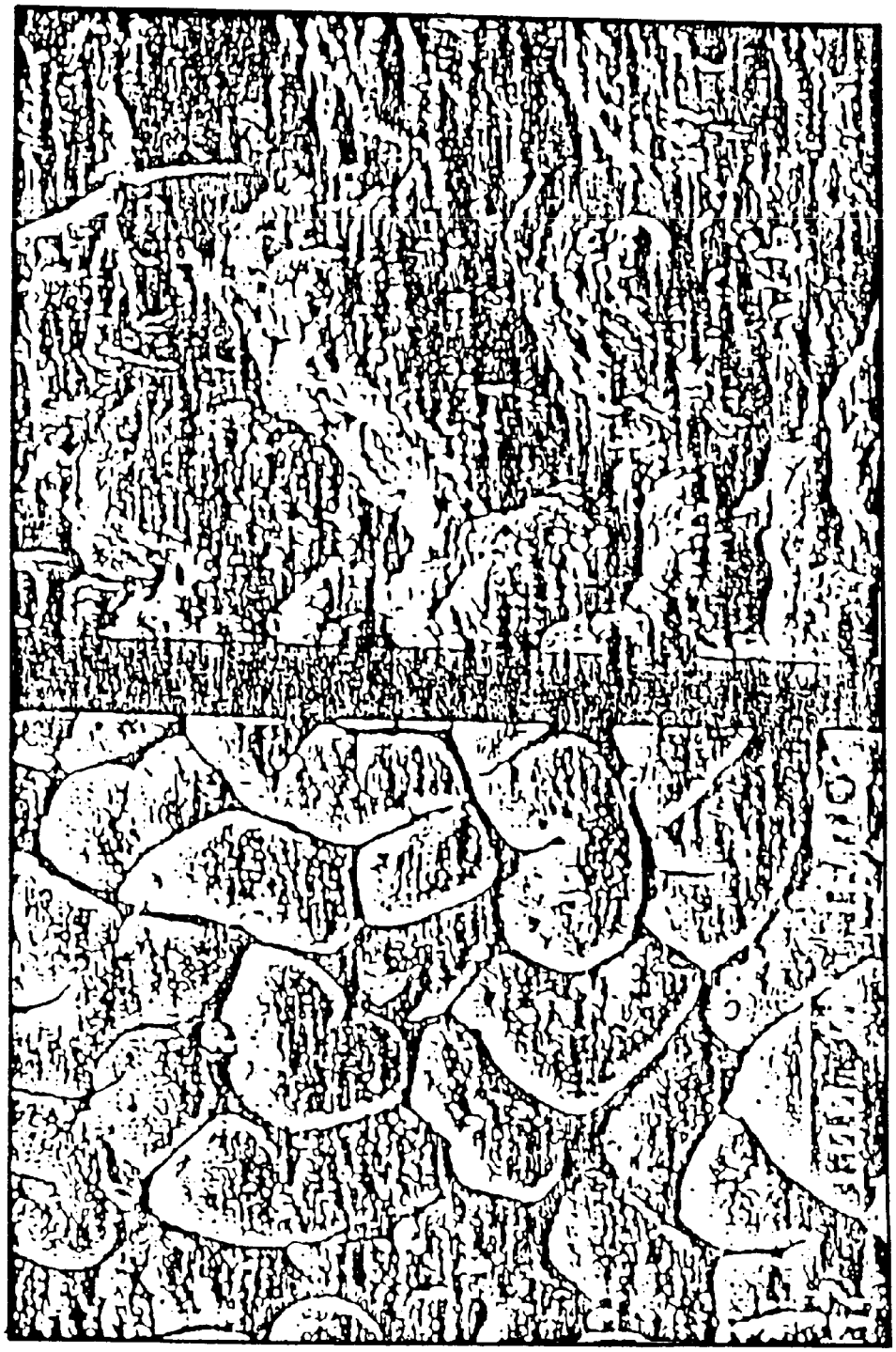
FIG. 6 shows an electron micrograph of the surface of the stomach antrum in dogs (a) (left side) not immunized (control) and (b) (right side) immunized with human gamma globulin (HGG) after intragastric administration of HGG (note surface coating in surface of stomach antrum of immunized dog).

Light microscopy and electron microscopy observations indicated there was a substantial release of mucus into the lumen of the stomach within ten minutes after addition of HGG in immunized dogs. This release of mucus was so extensive that the mucosa was coated with a thick layer of mucus (FIG. 6). As indicated in FIG. 6, the surface of the antrum in immunized animals (b) became indistinct due to massive secretions of mucus while cells remain uncoated and clearly visible on the surface of the antrum of non-immunized animals.

Gastrointestinal Blood Flow

Figure 7A:
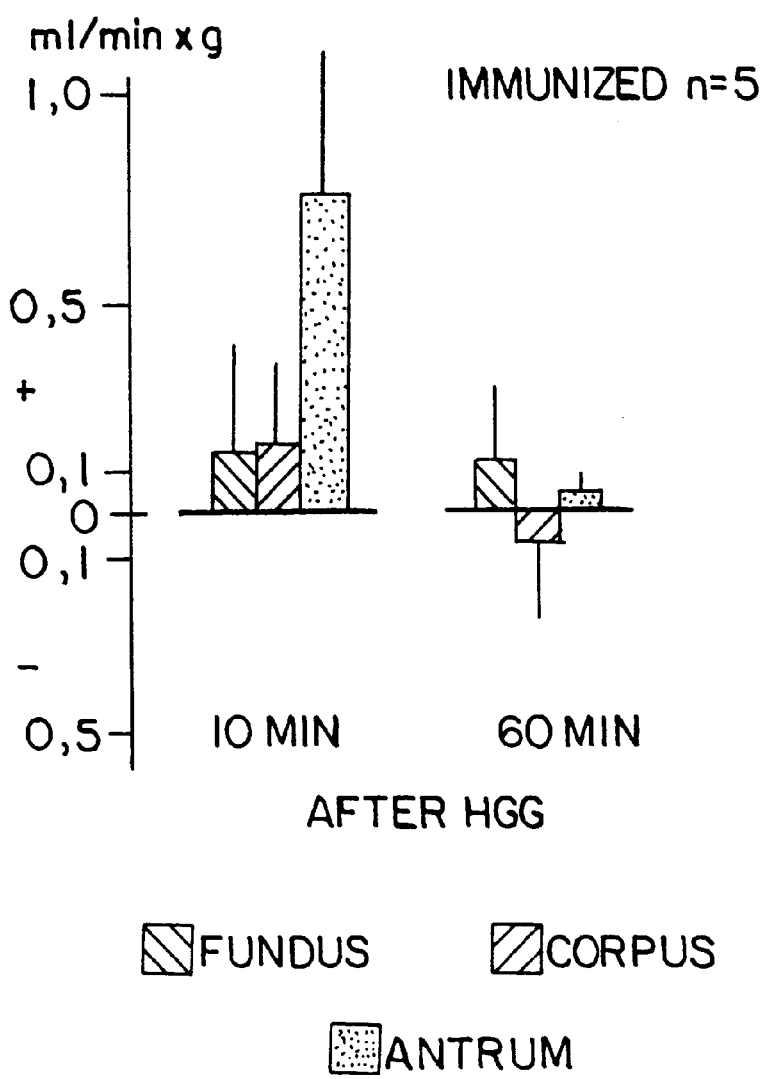
FIGS. 7a to 7c show blood flow changes in (a) gastric mucosa, (b) duodenum and pancreas, and (c) in the lower gut (mg/minxg) of dogs previously immunized with human gamma globulin (HGG) after intragastric administration of HGG.
Figure 7B:
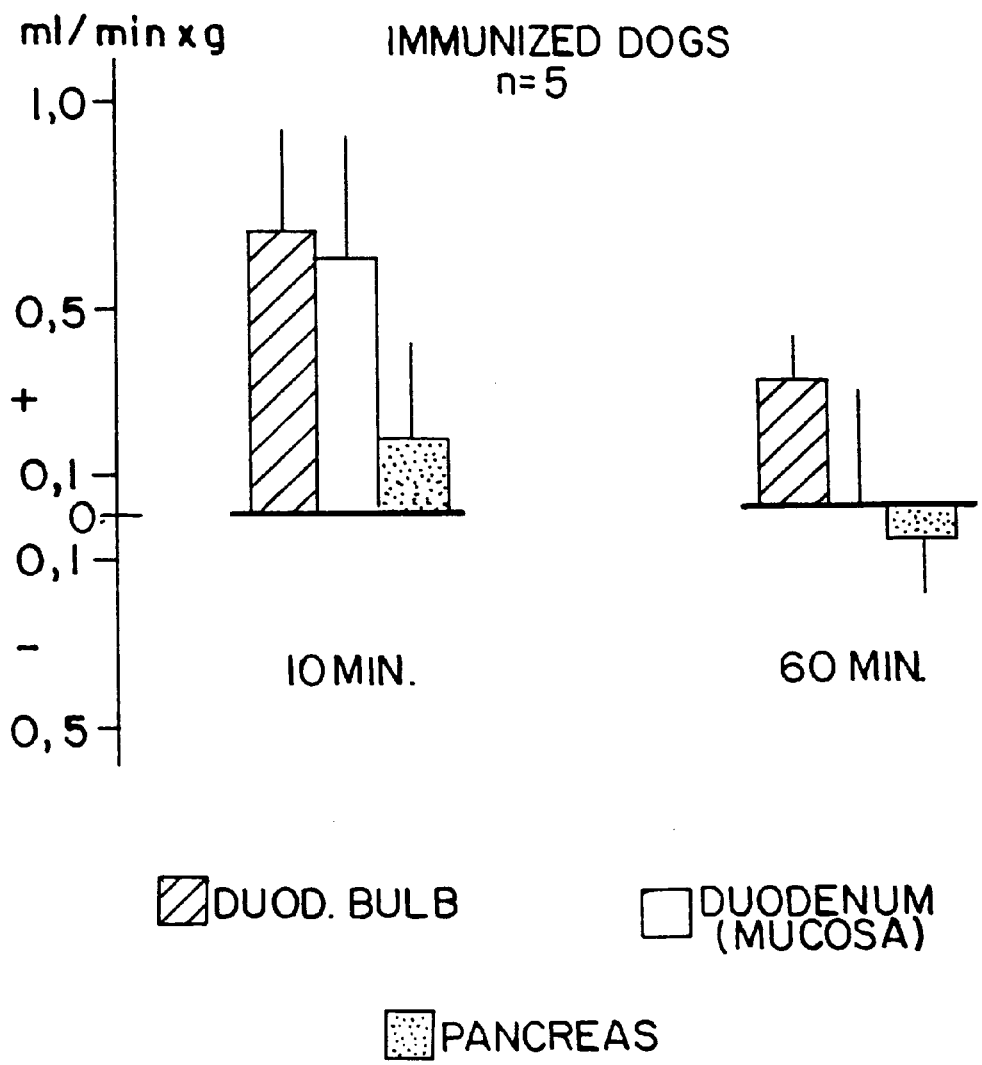
Figure 7C:
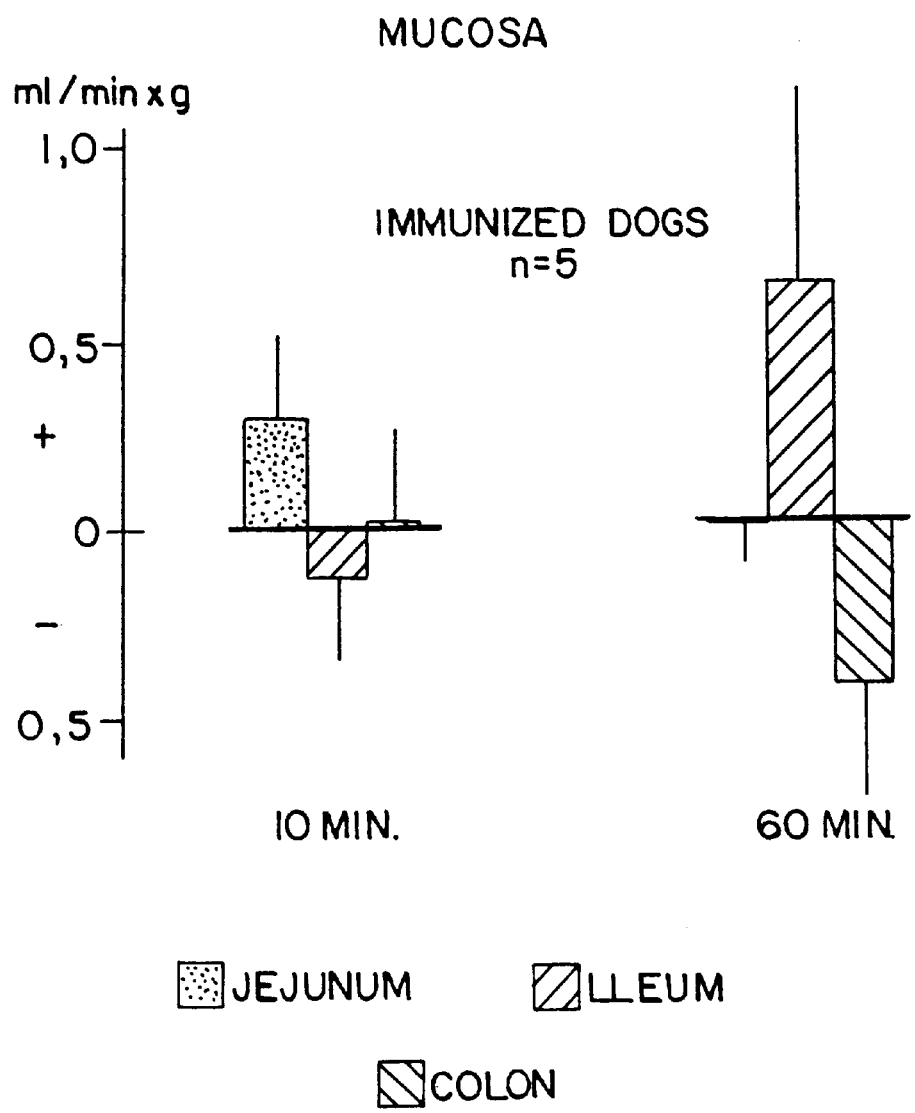

Changes in blood flow were measured as previously described (Teichmann, 1983a and Teichmann et al., 1983b), at 10 and 60 minutes after intragastric administration of HGG to immunized animals (FIG. 7a–c). Values were calculated by subtraction of basal flow values. Increased blood flow in the mucosa of the antrum, duodenal bulb, duodenum mucosa, pancreas and jejunum was observed at 10 min after administration of HGG. At 60 min, blood flow in the gastric mucosa returned to basal values while in the duodenal bulb, blood flow remained elevated. Moreover there was an increase in microcirculation within the ileum mucosa at 60 min.

Cardiovascular and Respiratory Parameters

There were no significant changes in heart minute volume, in blood pressure and blood gases in both immunized and non-immunized groups of dogs during the study.

Moreover, no influences on respiratory functions were observed.

B. Experiment 2

Stomach tissue was obtained from an animal and maintained in a perfusion chamber. Antigens, to which the animal had been or had not been previously exposed, were diffused into the perfusion chamber. After incubation for various periods of time with an antigen, stomach tissue was removed, immediately frozen and sectioned.

Lectin histochemistry was used to identify mucus secreting cells in the sectioned stomach tissue.

As depicted in FIG. 8 the diameter of secretory granules from immunized animals (black circles) decreased substantially within five minutes of exposure to an immunologically recognizable antigen, indicating that these granules had already released large amounts of mucus relative to non-immunized controls (open circles). Mucus was massively discharged from mucus-secreting cells in the glandular tubuli and volveolae as well as in superficial regions of the stomach wall. Moreover, sugar formation which is indicative of new mucus production, was detected within the cytoplasm and intracellular organelles like the Goigi apparatus, vesicles and vacuoles of cells. At about 90 minutes of antigenic exposure some of these cells exhibited negative lectin staining indicating that reserves of mucus had been released and no further mucus could be immediately synthesized.

Therefore, these experimental studies illustrate that increases in blood flow, mucus secretion and digestion regulatory factors like gastrin and secretin, can be immunologically stimulated by ingested antigens with which an animal is immunologically familiar.

EXAMPLE 7

IMMUNIZATION WITH SEVERAL TYPES OF ANTIGENS IN SEVERAL TYPES OF ANIMALS

The following in vitro experiments confirm that immunization of many types of animals with many types of antigens stimulates an immune response within the stomach wall, which initiates digestion. These studies demonstrate that a variety of antigens, including animal proteins, plant proteins, synthetic haptens, and microbially derived antigens can stimulate and control digestion via an immunological mechanism with the gastrointestinal tract.

An in vitro model was developed using small pieces of gastric mucosa obtained via biopsy, from surgical specimens or collected at the abattoir immediately after slaughter. Mucosa samples were placed in a perfusion chamber and washed with a buffered solution at body temperature. Mucosal secretion of gastric hormones such as gastrin and somatostatin was determined by detection of such hormones in the outflow solution from the perfusion chamber. The ingoing buffer solution was spiked with an antigen or other compound in order to evaluate the reaction of the gastric mucosa. In these studies, mucosal samples were obtained from animals or humans which previously had or had not been immunized with an antigen. Mucosal samples were then challenged with the same antigen used for immunization and the release of gastrin and somatostatin was detected in the chamber's outflow as a measure of resulting digestive events.

In all studies, the immunized animals were tested for the presence of circulating antibodies by ouchterlony tests of the animal's serum to confirm the presence of antibodies reactive with the immunizing antigen prior to obtaining a mucosa sample.

Table 7 illustrates various specific antigens that stimulated gastrin release in humans, dogs, pigs, cows, horses, chickens, fish, and rats.

TABLE 7

| \multicolumn{2}{c}{Antigens Stimulating Gastrin Release} | |
| --- | --- |
| Species | Substances |
| Dog | heart (beef) |
|  | fish |
|  | mixed offal proteins |
|  | wheat gluten |
|  | actin |
|  | synthetic actin peptide |
|  | myosin |
|  | synthetic myosin peptide |
| Human Being | liver extract |
|  | actin |
|  | tetanus-toxoid |
| Pig | potato |
|  | fish |
|  | ovalbumin |
|  | human albumin |
|  | actin |
|  | synthetic actin peptide |
|  | myosin |
|  | synthetic myosin peptide |
|  | light chain myosin |
|  | heavy chain myosin |
|  | sub-fragment 1 myosin |
|  | sub-fragment 2 myosin |
|  | interleukin-1 alpha |
|  | interleukin-2 |
|  | interleukin-4 |
| Cow | ovalbumin |
|  | soya |
|  | whole milk |
| Horse | complementary feed (chow) |
|  | oats |
|  | oat grits |
|  | wheat bran |
|  | malt germs |
|  | extraction grits |

TABLE 7-continued

Antigens Stimulating Gastrin Release

| Species | Substances |
|---|---|
| | wheat gluten |
| | ovalbumin |
| | corn grits |
| | rye |
| | barley |
| | wheat |
| Chicken | complementary feed (chow) |
| | wheat |
| | corn |
| Fish (Trout) | complementary feed (chow) |
| Rat | NIP (4-hydroxy-3-iodo-5-nitrophenyl acetic acid) |
| | interleukin-1 |
| | interleukin-2 |

PIGS

Prior Immunization with a Plant Protein Stimulates Digestion

Figure 9A:
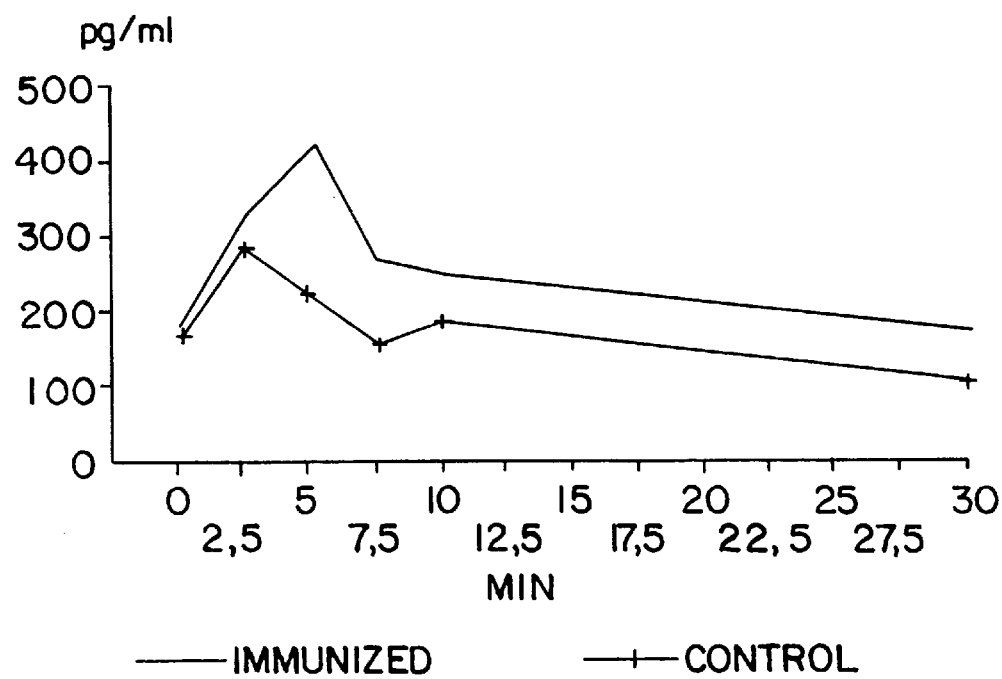
FIGS. 9a and 9b show total in vitro gastrin release (b) and in vitro gastrin release with time (a) (pg/ml vs. min.) in the gastric mucosa of pigs previously immunized with soy, as compared to non-immunized control pig gastric mucosa, upon in vitro exposure of these gastric mucosa to soy.
Figure 9B:
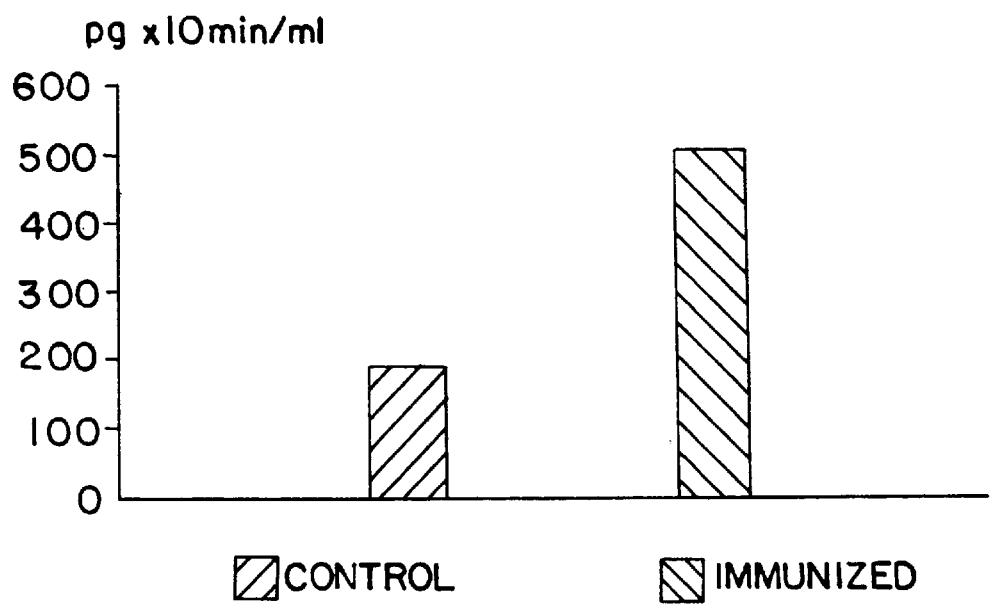

Pigs were parenterally immunized with soy (i.e. a plant antigen); control pigs were not immunized. Pieces of stomach wall tissue were harvested from pigs by gastroscopy and kept viable in a perfusion chamber. Soy was added to the input buffer of the perfusion chamber for 10 minutes. Gastrin was then measured in the chamber's outflow as an indicator for immunological and digestive stimulation. As shown in FIG. 9a, previously immunized animals had a significantly higher release of gastrin when compared with non-immunized control animals (about 250%). FIG. 9b depicts the integrated values for gastrin over the entire 10 minute stimulation period. This data demonstrated a significantly increased release of gastrin for immunized animals as opposed to controls. Moreover, this data confirm that immune cells within the gastric mucosa recognize known antigens and stimulate digestion upon such recognition.

Prior Immunization with Actin or Actin Synthetic Peptide Stimulates Digestion

Figure 17:
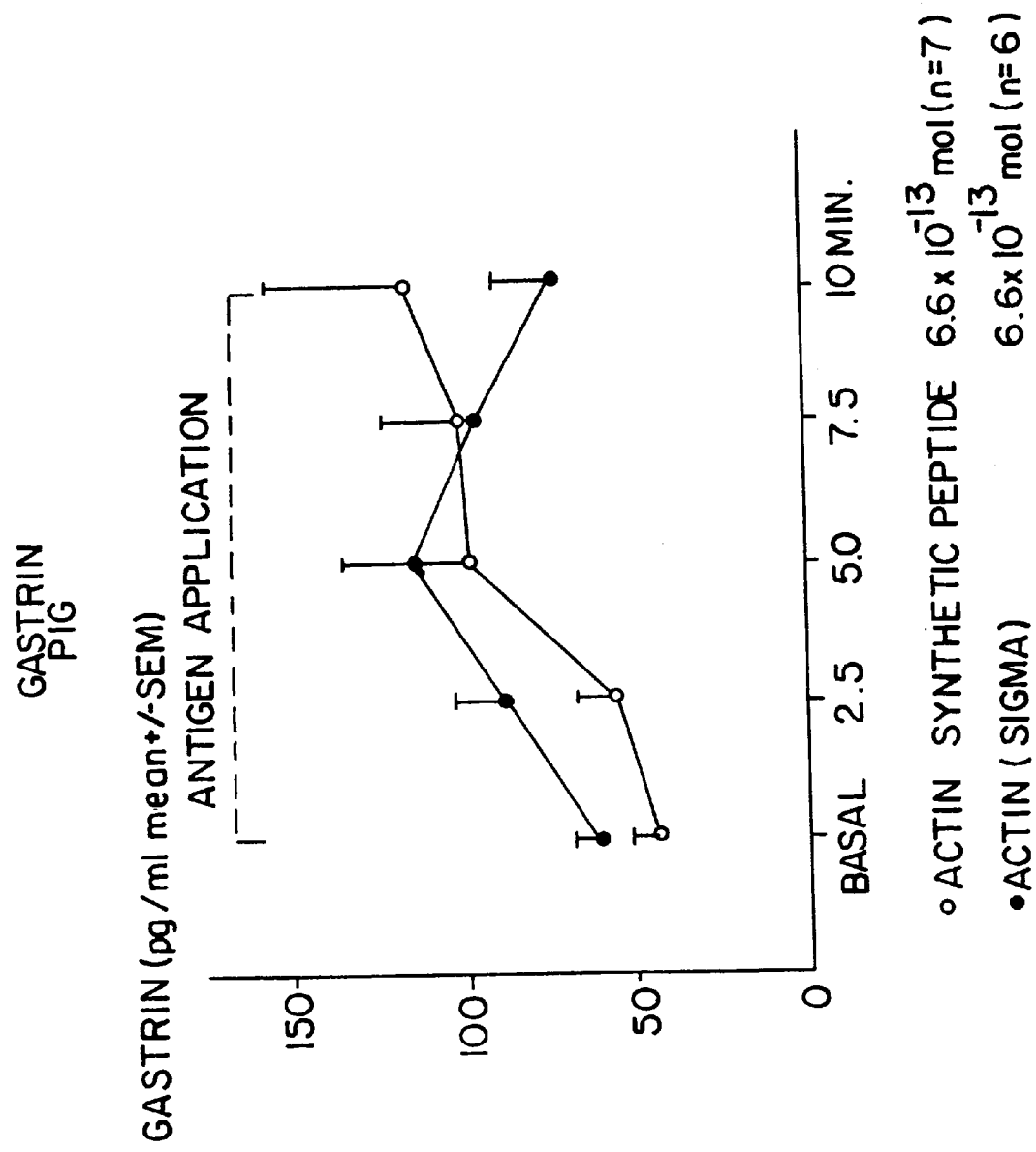
FIG. 17 shows gastrin release over course of antigen application in in vitro model in pig (pg/ml mean+/−SEM vs. time in min; open circle is actin synthetic peptide, $6.6 \times 10^{13}$ mol (n=7), darkened circle is actin (Sigma) $6.6 \times 10^{13}$ mol (n=6))

In this study, mucosal samples were obtained from pigs which previously had been immunized with Actin or an Actin Synthetic peptide and compared to a control group which had not been so immunized. Small pieces of gastric mucosa were obtained via biopsy and placed in a perfusion chamber. Mucosal secretion of gastrin was determined by detection of such hormones in the outflow solution from the perfusion chamber. As indicated in FIG. 17, the amount of gastrin (pg/ml) was measured in intervals of 2.5 minutes.

The results indicate that those mucosal samples challenged with Actin or the Actin Synthetic Peptide showed elevated gastrin secretion.

Prior Immunization with Myosin or Myosin Synthetic Peptide Stimulates Digestion

Figure 18:
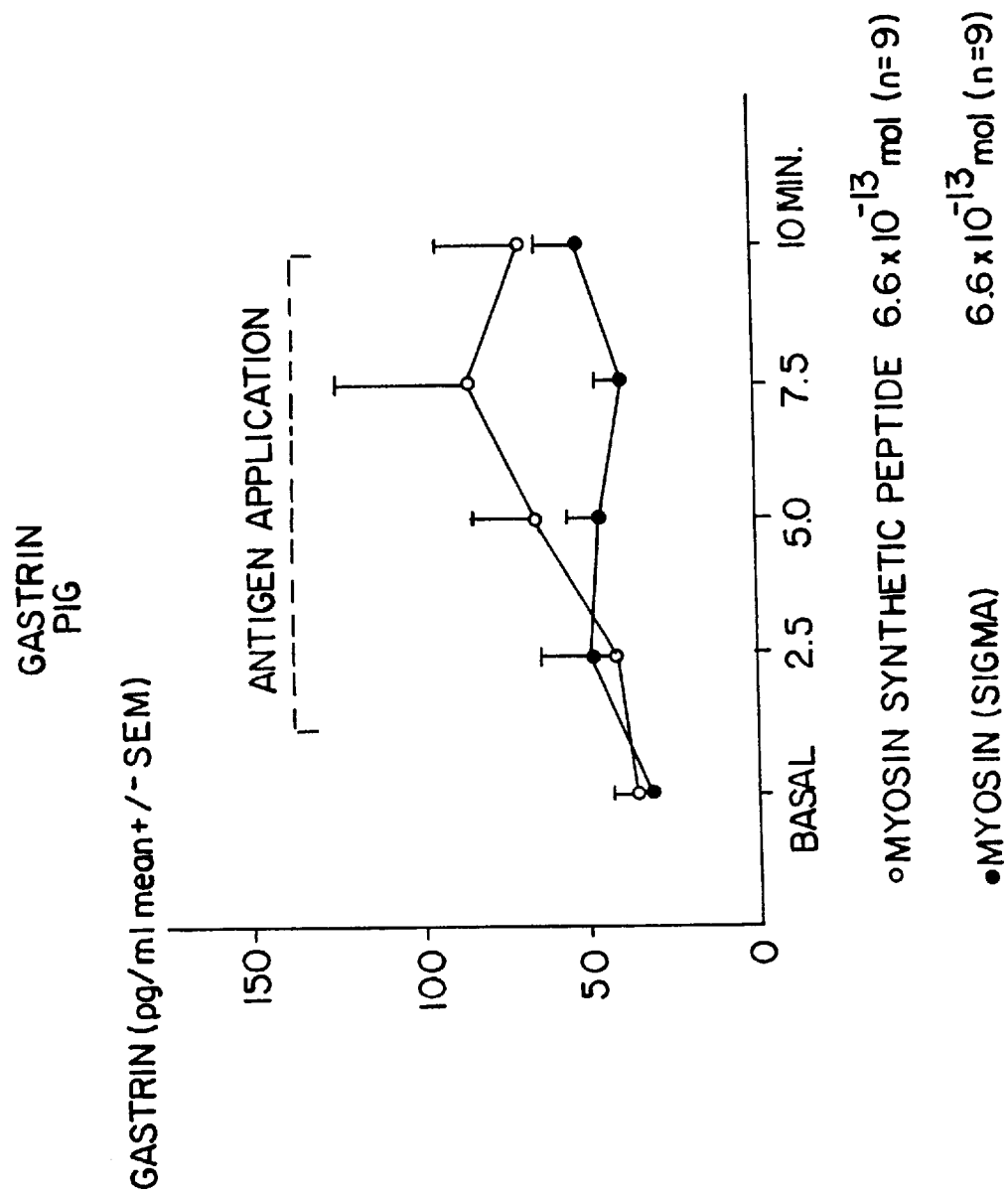
FIG. 18 shows gastrin release over course of antigen application in in vitro model in pig (pg/ml mean+/−SEM vs. time in min; open circle is myosin synthetic peptide, $6.6 \times 10^{13}$ mol (n=9), darkened circle is myosin (Sigma) $6.6 \times 10^{13}$ mol (n=9))

Using an identical experimental protocol, nine pigs were parenterally immunized with myosin; nine pigs were likewise immunized with myosin synthetic peptide; and a similar group for control pigs were not immunized. An in vitro model was developed by extracting pieces of stomach wall tissue by gastroscopy and placing them in a perfusion chamber. Myosin (or Myosin Synthetic Peptide) was added to the input buffer of the perfusion chamber for 10 minutes. Gastrin was then measured in the chamber's outflow (2.5 minute intervals) as an indicator for immunological and digestive stimulation. As shown in FIG. 18, animals previously immunized with the antigen had an increased release of gastrin over the 10 minute stimulation period. This data illustrate that immune cells within the gastric mucosa recognize known antigens (myosin or actin) and stimulate digestion upon such recognition.

DOGS

Figure 19:
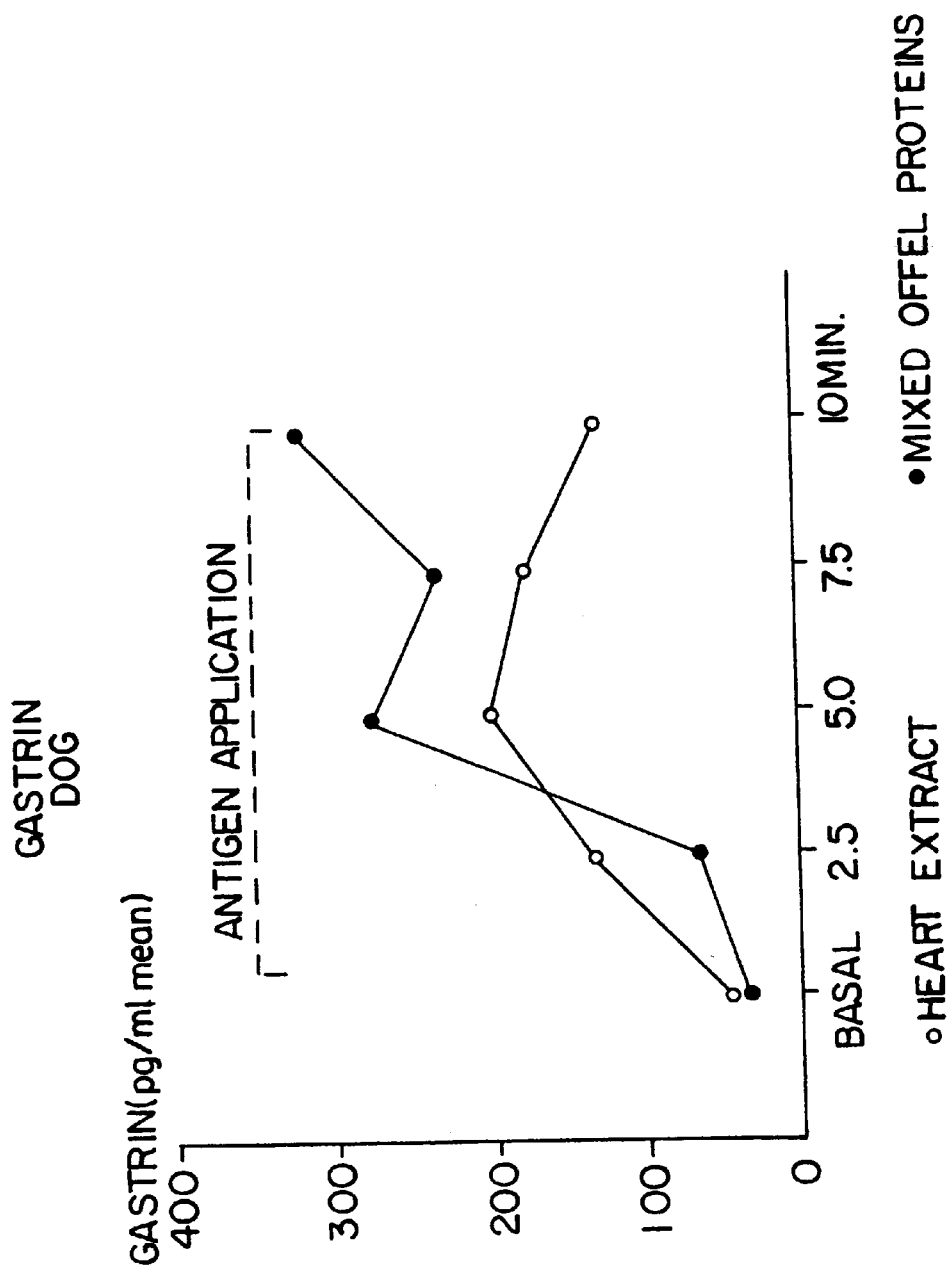
FIG. 19 shows gastrin release over course of antigen application in in vitro model in dog (pg/ml mean; open circle is heart extract, darkened circle is mixed olfal proteins); and, FIG. 20 shows gastrin release over course of antigen application in in vitro model in horse (pg/ml mean; open circle is basic food (chow), darkened circle is malt extract).

Prior Immunization with Antiaens Such As Heat Extract or Mixed Offal Proteins Stimulates Digestion This experiment conducted on dogs further shows that digestion regulatory factors such as gastrin can be immunologically stimulated by ingested antigens with which an animal is immunologically familiar. One group of dogs was parenterally immunized with heart extract, while another with mixed offal proteins. The amount of gastrin, secreted by the gastric mucosa extracted from the dogs and maintained in vitro, was measured over a ten minute time at 2.5 minute intervals. As illustrated in FIG. 19, immunization of dogs with heart extract or mixed offal proteins can stimulate gastrin and thereby control digestion via an immunological mechanism in the gastrointestinal tract.

HORSES

Prior Immunization with a Malt Extract or Basic Food Antigen Stimulates Digestion In this experiment, two groups of horses were parenterally immunized with two antigens; some with a basic food (chow) antigen and others with malt extract. Mucosal tissue from the stomach wall was harvested from horses and kept viable in a perfusion chamber. The antigens were added to the input butter of the perfusion chamber for 10 minutes. The amount of gastrin release by the tissue was then measured (in 2.5 minute intervals) in the chamber's outflow as an indicator for digestive stimulation. As shown in FIG. 20, those horses that were previously immunized with basic food antigen or the malt extract had increased levels of gastrin released during the 10 minute interval of antigen application. The experiment therefore confirms that the immune cells within the extracted tissue recognize known antigens and stimulate digestion upon recognition.

RATS

Prior Immunization with a Synthetic Hapten Stimulates Digestion

Figure 11:
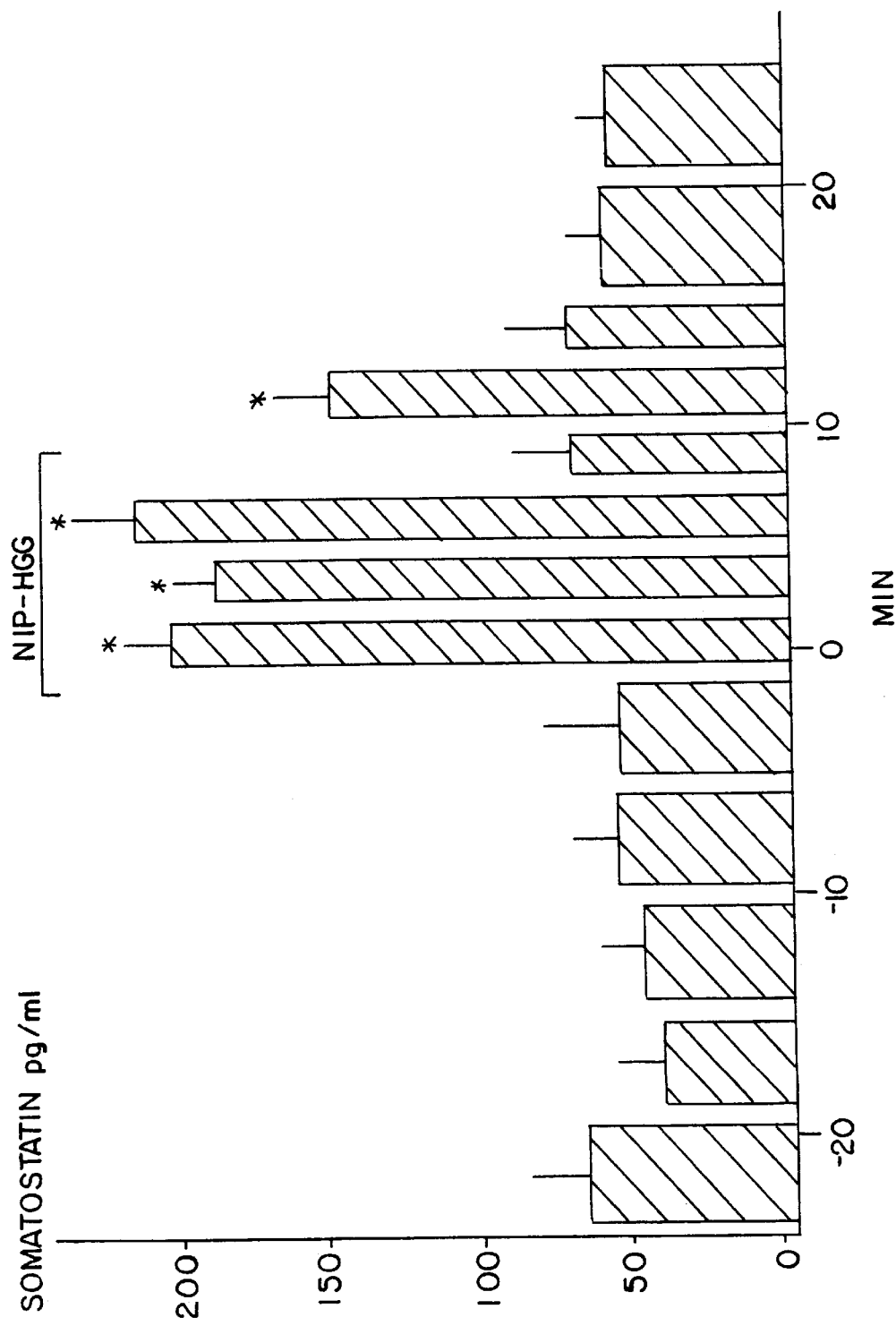
FIG. 11 shows the percent increase in somatostatin released from the gastric mucosa of rats previously immunized with a synthetic antigen, 4-hydroxy-3-iodo-nitrophenyl acetic acid (NIP), upon exposure of the mucosa in vitro to NIP bound to a carrier protein (NIP-HGG) (over time).

Rats were immunized with 4-hydroxy-3-iodo-nitrophenyl acetic acid (NIP) as a synthetic antigen. Gastric mucosa from non-immunized rats, challenged with NIP in the perfusion chamber, did not show any release of hormones. However, gastric mucosa from rats which had been immunized responded to NIP with a significant hormonal increase in both gastrin (FIG. 10) and somatostatin (FIG. 11). This study confirms that not only digestive stimulation (through release of gastrin) can be elicited by an immunological mechanism but also termination of digestion (through somatostatin) be elicited immunologically.

HUMANS

Prior Immunization with a Microbial Antigen Stimulates Digestion

Prior to surgery, patients requiring a gastrectomy were interviewed to ascertain whether or not they had been previously immunized against tetanus. If they had been vaccinated before, they received a booster injection 4 weeks before surgery. Mucosa from the antrum of surgically removed human stomachs was transferred to a perfusion chamber and challenged with tetanus toxoid (a microbial antigen). Mucosa from patients which had not been vaccinated against tetanus, and which had not received booster injections, served as a control.

Figure 12:
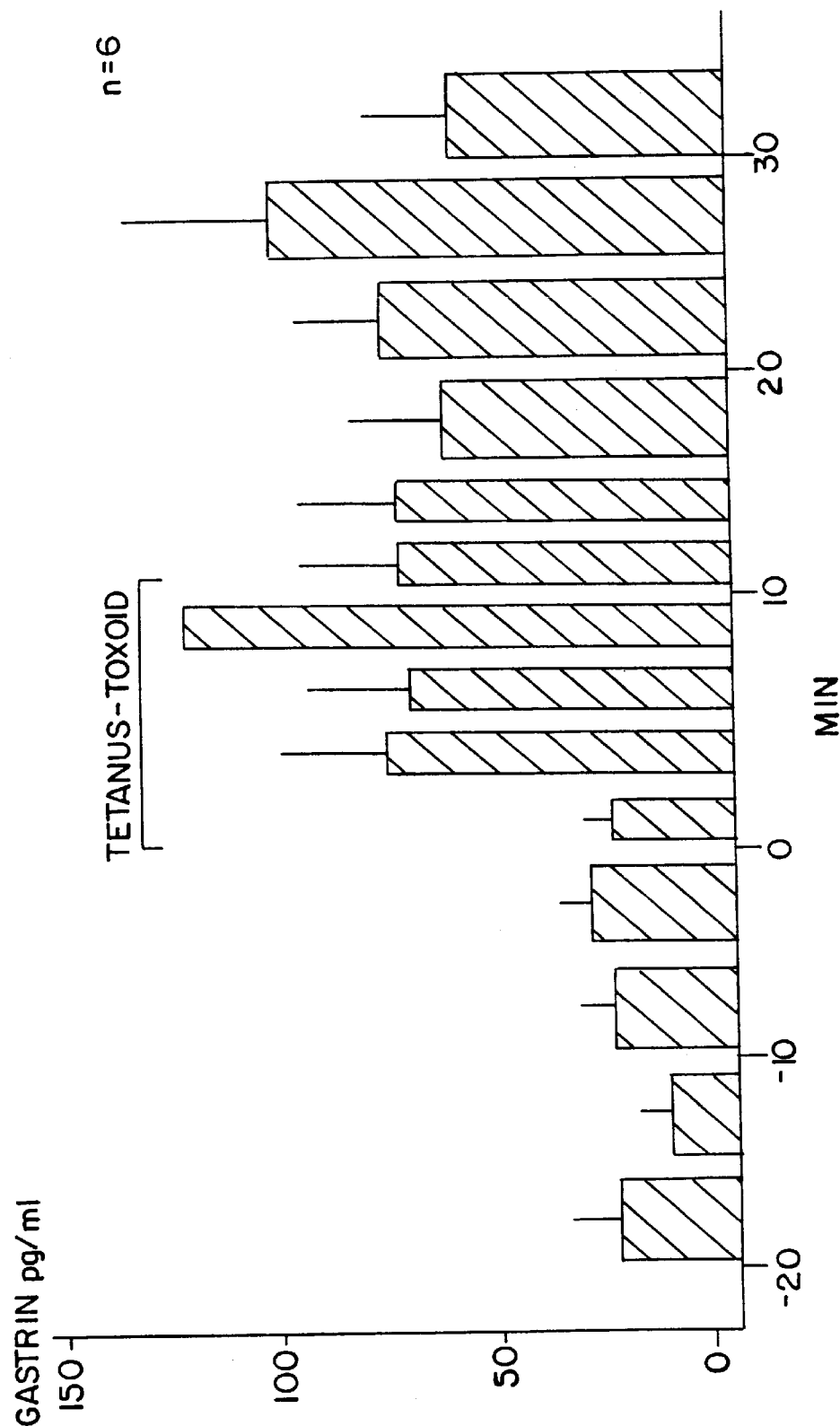
FIG. 12 shows the percent increase in gastrin released from the gastric mucosa of humans previously immunized with a microbial antigen, tetanus toxoid, upon in vitro exposure of the mucosa to this microbial antigen (over time) (Mucosa specimens from six patients were tested (i.e. n=6))
Figure 13:
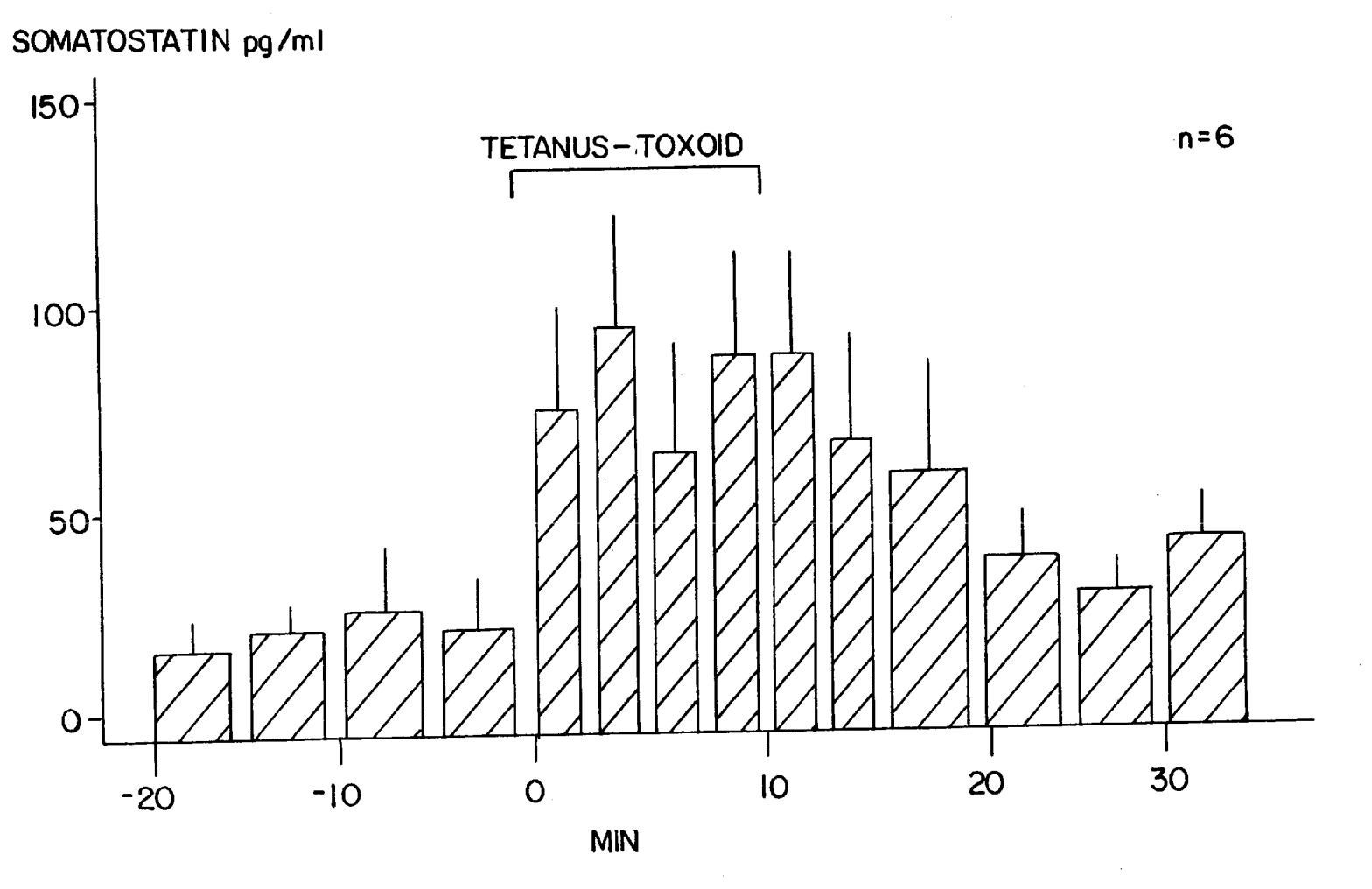

As shown in FIG. 12 and FIG. 13, there was a significant release of the hormones gastrin and somatostatin from the mucosa of patients which had been previously immunized in response to tetanus toxoid. Hormone release was observed in tissue of non-vaccinated patients when exposed to tetanus toxoid. Significantly, this is the first investigation confirming the existence of local immunological (antigen-antibody) reactions in the human gastric mucosa, following immunization with the antigen, which resulted in release of hormones capable of initiating and controlling the 'digestive cascade' (or gastric cascade).

EXAMPLE 8

ANTIBODY-PRODUCING CELLS IN THE STOMACH WALL STIMULATE DIGESTION UPON RECOGNITION OF AN ANTIGEN

Cells were obtained from the antral stomach wall of pigs previously immunized with actin and suspended in a perfusion chamber. Cells within such an antral cell suspension released gastrin when the suspension was exposed to actin. After irradiation of the suspension at dosages lethal to lymphocytes but not lethal to gastric wall cells, actin exposure no longer elicited gastrin release. However, stimulation of cells in the irradiated suspension with the neurotransmitter bombesin or with peptone elicited gastrin release, indicating these gastrin releasing cells were alive and functional.

These results demonstrate that gastrin-releasing cells are stimulated to release gastrin by immune cells in the stomach wall.

EXAMPLE 9

PREPARATION OF INGESTIBLE ANTIGENS FOR IMMUNIZATION AND ORAL REINTRODUCTION INTO YOUNG ANIMALS

Whey:
1. Native whey (sweet or sour) with a protein content of 0.9%, was concentrated by sedimentation (4° C.) and subsequent centrifugation (20° C.) to produce a 10% protein solution, which was sterilized by filtration through a 0.2 um filter. Sterility was tested under guidelines established by APHIS, USDA and/or FDA. The solution was placed into sterile glass vials and sealed with crimped rubber stoppers using sterile techniques. Protein content was assayed by standard procedures, e.g., the bicinchoninic acid (BCA) method.

2. Heat dried whey was used to prepare a solution containing 10% protein by suspension in distilled water with subsequent sedimentation, centrifugation and sterile filtration followed by placement into vials and capping by sterile techniques.

Immunization:
One ml of whey-derived 10% protein solution was injected in piglets intramuscularly, subcutaneously or intraperitoneally at 28, 49 and 70 days of age.

Oral Reintroduction:
Only whey of the same origin as the whey used for immunization i.e. fresh sweet, or fresh sour, or heat dried whey, respectively, was used for oral reintroduction. For example, piglets immunized with fresh sour whey were orally reintroduced to fresh sour whey, and not to fresh sweet whey or heat dried whey. Fresh whey was used as a replacement for drinking water. In separate tests, heat dried whey was incorporated into the diet. Both methods of oral reintroduction were maintained consistently throughout outgrowth and finishing periods, until slaughter.

Soy:
1. Toasted soy flour, containing either 44% or 48% protein (called soy 44 or 48) or highly purified soy preparations (soy meals) containing 90% protein or more were milled in a ball mill and put through a sieve with pores of less than 0.06 mm. One part of this soy meal was suspended in five parts of aluminum hydroxide gel at temperatures between 20° and 30° C. This preparation contained 85 mg/ml soy protein. Formaldehyde can be used a sterilizing agent. However, it is preferred that only freshly prepared material be used.

Piglets were subcutaneously injected with 1 or 2 ml of this preparation at the age of 21, 35 and 49 days. This formulation can result in tissue reactions. The following preparation was free of tissue reactions.

2. Toasted soy flour, containing either 44% or 48% protein (called soy 44 or 48) or highly purified soy preparations (soy meals) containing 90% or more protein was used. One part soy was added to seven parts of purified water (USP), for example, 1000 g soy flour was added to 7 liters of water. Further water (3 parts) was added after the soy was in solution. After stirring at room temperature for one hour the solution was centrifuged and sterilized by filtration using a 0.2 um filter. The sterile solution containing 10±1.0 mg/ml protein, was placed in vials and capped using sterile techniques. This preparation was sterile and free of side effects of when given parenterally to piglets, lambs, calves or chickens. Moreover, a detectable reaction was observed between these soy antigens and antibodies using Western blot methodology. Approved stabilizing agents were added as needed.

Piglets were immunized with subcutaneously and/or intramuscularly 1 or 2 ml of the soy antigens at the age of 21, 35 and 49 days, or at 28, 49 and 70 days of age. In calves, lambs and kids, immunization was subcutaneous and/or intramuscular with 1 or 2 ml at the ages of 21, 42 and 63 days, or at 28, 49 and 70 days, or at 21, 35 and 49 days of age.

Oral Reintroduction:
Soy 44, soy 48 or soy with greater than 90% protein was used as part of the daily diet, in concentrations ranging, and increasing over time, from 1% to 30%, from weaning to slaughter.

METHODS FOR ORAL VACCINATION

Immunization:
Piglets at 7 to 10 days of age received creep feed with about 5–10% soy 44 or 48. The soy 44 or 48 content in the diet was then elevated weekly in step-wise fashion to 30% of the diet at the age of 28 to 30 days.

Oral Reintroduction:
For the rest of their lives, pigs received a diet with 15 to 30% soy protein. 10 to 100 times more soy protein was needed for oral immunization when compared with parenteral immunization.

In a similar fashion, calves, lambs and kids were orally immunized at 7 to 19 days of age with soy protein in increasing concentrations in a milk replacer diet or as creep feed.

Oral immunization is the route of choice for broiler chickens and turkeys using soy in low concentrations in starter diets and increasing levels in maintenance diets for systematic oral reintroduction.

Cultured fish fingerlings in tanks and raceways (long holding tank in hatchery) are also orally immunized by initial low doses of soy protein in starter feeds and increasing levels in maintenance diets for optimal oral immunization and reintroduction.

Corn or Sorghum Protein:

Methods similar to those described above for soy are used to prepare protein solutions from corn (maize) and sorghum, with corn or sorghum flour as a starting material.

Preferably, soy, sorghum and corn derived protein solutions for immunization of livestock are prepared from raw materials of different origins and mixed, thus producing polyvalent antigen preparations. This procedure assures an overlap between orally reintroduced proteins in soy, sorghum and corn feed which can differ in origin from the material used for initial immunization.

Having thus described in detail the preferred embodiments of the present invention, it is to be understood that the invention defined by the appended claims is not to be limited by particular details set forth in the above description as many apparent variations thereof are possible without departing from the spirit or scope of the present invention.

What is claimed:

1. A process to improve nutrient utilization in an animal or human by stimulating a gastric cascade in the animal or human, said process to improve nutrient utilization comprising:

immunizing the animal or human orally or parenterally with an antigen; and reintroducing the antigen orally effective to stimulate a gastric cascade, wherein said gastric cascade includes i) initiating digestion, ii) stimulating the secretion of digestive acids and enzymes within the gastrointestinal tract, iii) increasing the blood flow to the stomach, and iv) stimulating the production of mucus, wherein the gastric cascade is effective to improve nutrient utilization by the animal or human.

2. The process according to claim 1 wherein the antigen is selected from the group consisting of amino acids, peptides, proteins, scleroproteins, globular proteins, histones, albumins, globulins, and proteids.

3. The process according to claim 1 wherein the antigen is a synthetic peptide with antigenic determinants for stimulating an immune response.

4. The process according to claim 3 wherein the antigen is a hapten, selected from the group consisting of nitrophenylacetic acid and 2,4-dinitrofluorobenzene.

5. The process according to claim 1 wherein the antigen is a hapten coupled to a carrier protein.

6. The process according to claim 1 wherein in the immunizing step a quantity of antigen of 1 to 500 mg/kg of body weight is used.

7. The process according to claim 6 wherein in the immunizing step the antigen is applied once or several times parenterally in a quantity of 1 to 100 mg/kg of body weight.

8. The process according to claim 1 wherein in the reintroducing step the antigen is applied daily and in enteral manner in a quantity of 2 to 500 mg/kg of body weight.

9. The process of claim 1 wherein the antigen is whey.

10. The process of claim 9 wherein the animal is a pig.

11. The process of claim 1 wherein the animal is a dog.

12. The process of claim 1 wherein the animal is a rat.

13. The process of claim 1 further comprising applying the antigen gastrointestinally prior to immunizing the animal or human with the antigen.

14. The process of claim 1 further comprising applying the antigen gastrointestinally simultaneously with immunizing the animal or human with the antigen.

15. A process for improving nutrient utilization in an animal or a human by stimulating a gastric cascade in the animal or human, said process comprising applying an antigen gastrointestinally effective to stimulate a gastric cascade after immunization has been achieved by the antigen, wherein said gastric cascade includes i) initiating digestion, ii) stimulating the secretion of digestive acids and enzymes within the gastrointestinal tract, iii) increasing the blood flow to the stomach, and iv) stimulating the production of mucus.

16. The process according to claim 15 wherein the antigen is selected from the group consisting of amino acids, peptides, proteins, scleroproteins, globular proteins, histones, albumins, globulins, and proteids.

17. The process according to claim 15 wherein the antigen is a synthetic peptide with antigenic determinants for stimulating an immune response.

18. The process according to claim 17 wherein the antigen is a hapten, selected from the group consisting of nitrophenylacetic acid and 2,4-dinitrofluorobenzene.

19. The process according to claim 15 wherein the antigen is a hapten coupled to a carrier protein.

20. The process according to claim 15 wherein the immunization is achieved by a quantity of antigen of 1 to 500 mg/kg of body weight is used.

21. The process according to claim 20 wherein the immunization is achieved by administration of the antigen once or several times parenterally in a quantity of 1 to 100 mg/kg of body weight.

22. The process according to claim 15 wherein in the applying step the antigen is applied daily and in enteral manner in a quantity of 2 to 500 mg/kg of body weight.

23. The process of claim 15 wherein the antigen is whey.

24. The process of claim 23 wherein the animal is a pig.

25. The process of claim 15 wherein the animal is a dog.

26. The process of claim 15 wherein the animal is a rat.

* * * * *